(12) United States Patent
Jung et al.

(10) Patent No.: US 9,450,190 B2
(45) Date of Patent: Sep. 20, 2016

(54) CONDENSED CYCLIC COMPOUND AND ORGANIC LIGHT-EMITTING DIODE INCLUDING THE SAME

(71) Applicant: SAMSUNG DISPLAY CO., LTD., Yongin, Gyeonggi-Do (KR)

(72) Inventors: Hye-Jin Jung, Yongin (KR); Jin-O Lim, Yongin (KR); Sang-Hyun Han, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 86 days.

(21) Appl. No.: 14/297,585

(22) Filed: Jun. 5, 2014

(65) Prior Publication Data

US 2015/0162541 A1   Jun. 11, 2015

(30) Foreign Application Priority Data

Dec. 6, 2013   (KR) ................. 10-2013-0151345

(51) Int. Cl.
*H01L 51/00* (2006.01)
*C09B 5/00* (2006.01)
(Continued)

(52) U.S. Cl.
CPC ......... *H01L 51/0061* (2013.01); *C07C 211/55* (2013.01); *C07C 211/61* (2013.01);
(Continued)

(58) Field of Classification Search
CPC ........... H01L 51/5056; H01L 51/5072; C07C 211/61; C07C 211/55
USPC .......................................... 548/418; 257/258
See application file for complete search history.

(56) References Cited

U.S. PATENT DOCUMENTS 6,329,086 B1 * 12/2001 Shi .................. C09K 11/06
                                                        252/301.16

7,053,255 B2   5/2006 Ikeda et al.
(Continued)

FOREIGN PATENT DOCUMENTS

JP         2009-099658 A    5/2009
KR   10-2006-0006760 A      1/2006
(Continued)

OTHER PUBLICATIONS

Donaghey, Jenny E. et al., Pyrroloindacenodithiophene containing polymers for organic field effect transistors and organic photovoltaics; journal, Oct. 10, 2011, 9 pages, J. Mater, Chem., 2011, 21, The Royal Society of Chemistry 2011.
(Continued)

*Primary Examiner* — Caridad Everhart
(74) *Attorney, Agent, or Firm* — Lewis Roca Rothgerber Christie LLP

(57) ABSTRACT

A condensed cyclic compound is represented by Formula 1, and an organic light-emitting diode includes the condensed cyclic compound:

Formula 1

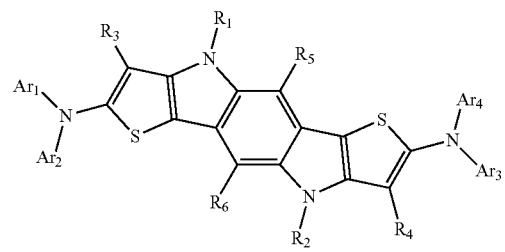

wherein, in Formula 1, the descriptions of $Ar_1$ to $Ar_4$, and $R_1$ to $R_6$ are as defined in the present specification. An organic light-emitting diode including an organic layer including the condensed cyclic compound may have a low driving voltage, a high light-emitting efficiency, and a long lifespan.

20 Claims, 1 Drawing Sheet

(51) Int. Cl.
*C07C 211/55* (2006.01)
*C07C 211/61* (2006.01)
*H01L 51/50* (2006.01)

(52) U.S. Cl.
CPC ....... H01L51/0071 (2013.01); H01L 51/0073 (2013.01); *H01L 51/0081* (2013.01); *H01L 51/5012* (2013.01)

(56) References Cited

U.S. PATENT DOCUMENTS

| | | | |
|---|---|---|---|
| 7,233,019 B2 | 6/2007 | Ionkin et al. | |
| 2005/0156164 A1 | 7/2005 | Sotoyama | |
| 2006/0063037 A1 | 3/2006 | Kim et al. | |
| 2009/0026935 A1 | 1/2009 | Matsunami et al. | |
| 2011/0087034 A1 | 4/2011 | Miyata et al. | |
| 2011/0166362 A1* | 7/2011 | Miyata | C07D 495/04 548/417 |
| 2012/0184089 A1* | 7/2012 | Zuberi | C07D 495/04 438/478 |
| 2013/0069020 A1* | 3/2013 | May | C09K 11/06 252/519.21 |
| 2013/0323913 A1* | 12/2013 | Miyata | H01L 51/0071 438/479 |
| 2013/0324716 A1* | 12/2013 | Brown | H01L 51/006 544/35 |
| 2014/0158949 A1* | 6/2014 | Wang | C07D 495/22 252/511 |

FOREIGN PATENT DOCUMENTS

| | | |
|---|---|---|
| KR | 10-2009-0010883 A | 1/2009 |
| KR | 10-2010-0117068 A | 11/2010 |
| KR | 10-2012-0097320 A | 9/2012 |

OTHER PUBLICATIONS

Xiong, Yu et al., Electron-Rich Pyrroloindacenodithiophenes: Synthesis, Characterization, and Spectroscopic Studies, journal, 5 pages, J. Org, Chem. 2013, 2012 American Chemical Society.

* cited by examiner

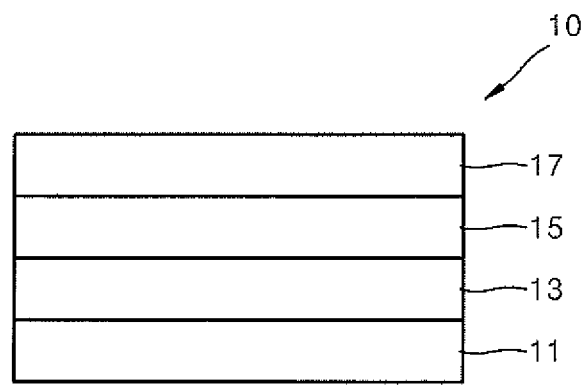

CONDENSED CYCLIC COMPOUND AND ORGANIC LIGHT-EMITTING DIODE INCLUDING THE SAME

CROSS-REFERENCE TO RELATED APPLICATION

This application claims priority to and the benefit of Korean Patent Application No. 10-2013-0151345, filed on Dec. 6, 2013, in the Korean Intellectual Property Office, the disclosure of which is incorporated herein in its entirety by reference.

BACKGROUND

1. Field

One or more embodiments of the present invention relate to a condensed cyclic compound and an organic light-emitting diode including the same.

2. Description of the Related Art

Organic light-emitting diodes (OLEDs), which are self-emitting devices, have desired features such as wide viewing angles, excellent contrast, quick response, high luminance, excellent driving voltage characteristics, etc., and can provide multicolored images.

The OLED has a structure including a first electrode, a hole transport region, an emission layer, an electron transport region, and a second electrode, which are sequentially stacked on a substrate. Holes injected through the first electrode move to the emission layer via the hole transport region, and electrons injected through the second electrode move to the emission layer via the electron transport region. Carriers such as the holes and electrons recombine in the EML to generate excitons. When the exitons drop from an excited state to a ground state, light is emitted.

SUMMARY

Aspects according to one or more embodiments of the present invention are directed toward a novel condensed cyclic compound and an organic light-emitting diode including the same.

Additional aspects will be set forth in part in the description which follows and, in part, will be apparent from the description, or may be learned by practice of the presented embodiments.

According to one or more embodiments of the present invention, a condensed cyclic compound is represented by Formula 1:

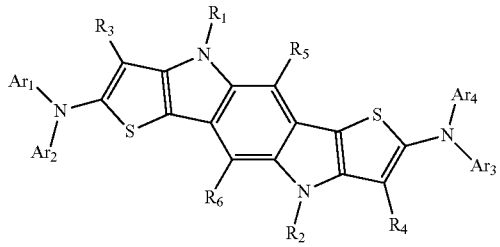

Formula 1 wherein, in Formula 1, $Ar_1$ to $Ar_4$ are each independently selected from a substituted or unsubstituted $C_6$-$C_{30}$ aryl group, a substituted or unsubstituted $C_4$-$C_{30}$ heteroaryl group, and a substituted or unsubstituted monovalent $C_6$-$C_{30}$ non-aromatic condensed polycyclic group;

$R_1$ and $R_2$ are each independently selected from a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, —Si($Q_1$)($Q_2$)($Q_3$), and —B($Q_4$)($Q_5$);

$R_3$ to $R_6$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, —Si($Q_1$)($Q_2$)($Q_3$), and —B($Q_4$)($Q_5$), wherein at least one substituent of the substituted $C_1$-$C_{10}$ alkyl group, substituted $C_2$-$C_{10}$ alkenyl group, substituted $C_2$-$C_{10}$ alkynyl group, substituted $C_1$-$C_{10}$ alkoxy group, substituted $C_3$-$C_{10}$ cycloalkyl group, substituted $C_3$-$C_{10}$ cycloalkenyl group, substituted $C_3$-$C_{10}$ heterocycloalkyl group, substituted $C_3$-$C_{10}$ heterocycloalkenyl group, substituted $C_6$-$C_{30}$ aryl group, substituted $C_2$-$C_{30}$ heteroaryl group, substituted $C_6$-$C_{30}$ aryloxy group, and substituted $C_6$-$C_{30}$ arylthio group is selected from:

a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, $-N(Q_{11})(Q_{12})$, $-Si(Q_{13})(Q_{14})(Q_{15})$, and $-B(Q_{16})(Q_{17})$;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, $-N(Q_{21})(Q_{22})$, $-Si(Q_{23})(Q_{24})(Q_{25})$, and $-B(Q_{26})(Q_{27})$; and $-Si(Q_{31})(Q_{32})(Q_{33})$ and $-B(Q_{34})(Q_{35})$;

$Q_1$ to $Q_5$, $Q_{11}$ to $Q_{17}$, $Q_{21}$ to $Q_{27}$, and $Q_{31}$ to $Q_{37}$ are each independently selected from a hydrogen atom, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

According to one or more embodiments of the present invention, an organic light-emitting diode includes a first electrode; a second electrode facing the first electrode; and an organic layer between the first electrode and the second electrode, and including an emission layer, wherein the organic layer includes at least one of the condensed cyclic compounds.

BRIEF DESCRIPTION OF THE DRAWING

These and/or other aspects will become apparent and more readily appreciated from the following description of the embodiments, taken in conjunction with the accompanying drawing in which:

The drawing schematically illustrates the structure of an organic light-emitting diode according to an embodiment of the present invention.

DETAILED DESCRIPTION

Reference will now be made in more detail to embodiments, examples of which are illustrated in the accompanying drawing, wherein like reference numerals refer to the like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention."

According to an embodiment of the present invention, a condensed cyclic compound is represented by Formula 1:

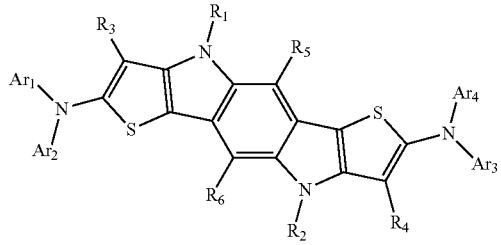

Formula 1

In Formula 1, $Ar_1$ to $Ar_4$ may be each independently selected from a substituted or unsubstituted $C_6$-$C_{30}$ aryl group, a substituted or unsubstituted $C_4$-$C_{30}$ heteroaryl group, and a substituted or unsubstituted monovalent $C_6$-$C_{30}$ non-aromatic condensed polycyclic group;

$R_1$ and $R_2$ may be each independently selected from a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, $-Si(C)_1)(Q_2)(Q_3)$, and $-B(Q_4)(Q_5)$;

$R_3$ to $R_6$ may be each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, monovalent $C_6$-$C_{30}$ non-aromatic condensed polycyclic group, $-Si(Q_1)(Q_2)(Q_3)$, and $-B(Q_4)(Q_5)$, wherein at least one substituent of the substituted $C_1$-$C_{10}$ alkyl group, substituted $C_2$-$C_{10}$ alkenyl group, substituted $C_2$-$C_{10}$ alkynyl group, substituted $C_1$-$C_{10}$ alkoxy group, substituted $C_3$-$C_{10}$ cycloalkyl group, substituted $C_3$-$C_{10}$ cycloalkenyl group, substituted $C_3$-$C_{10}$ heterocycloalkyl group, substituted $C_3$-$C_{10}$ heterocycloalkenyl group, substituted $C_6$-$C_{30}$ aryl group, substituted $C_2$-$C_{30}$ heteroaryl group, substituted $C_6$-$C_{30}$ aryloxy group, and substituted $C_6$-$C_{30}$ arylthio group may be selected from:

a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_5$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{21}$)($Q_{22}$), —Si($Q_{23}$)($Q_{24}$)($Q_{25}$), and —B($Q_{26}$)($Q_{27}$); and —Si($Q_{31}$)($Q_{32}$)($Q_{33}$) and —B($Q_{34}$)($Q_{35}$); and $Q_1$ to $Q_5$, $Q_{11}$ to $Q_{17}$, $Q_{21}$ to $Q_{27}$, and $Q_{31}$ to $Q_{37}$ may be each independently selected from a hydrogen atom, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

In one embodiment, $Ar_1$ to $Ar_4$ may be each independently selected from:

a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a phosphoric acid group or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_4$-$C_{30}$ heteroaryl group, a $C_6$-$C_{30}$ aryloxy group, and a $C_6$-$C_{30}$ arylthio group, and —Si($Q_{31}$)($Q_{32}$)($Q_{33}$) (where, $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group).

For example, in Formula 1, $Ar_1$ to $Ar_4$ may be each independently represented by one of Formulae 2A to 2D:

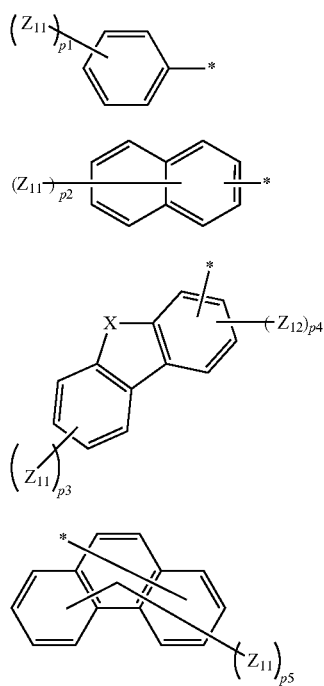

2A

2A

2C

2D

In Formulae 2A to 2D,

X may be O, S, or $C(Z_{12})(Z_{13})$;

$Z_{11}$ to $Z_{13}$ may be each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{30}$ aryl group, a $C_4$-$C_{30}$ heteroaryl group, and —$Si(Q_{31})(Q_{32})(Q_{33})$ (where, $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group);

p1 may be an integer selected from 1 to 5;

p2 may be an integer selected from 1 to 7;

p3 may be an integer selected from 1 to 4;

p4 may be an integer selected from 1 to 3; and p5 may be an integer selected from 1 to 9.

* is a binding site with a pyrroloindacenodithiophene core.

For example, in Formula 1, $Ar_1$ to $Ar_4$ may be each independently represented by one of Formulae 3A to 3R, but are not limited thereto:

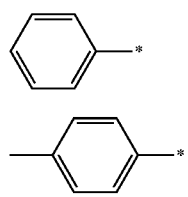

3A

3B

-continued

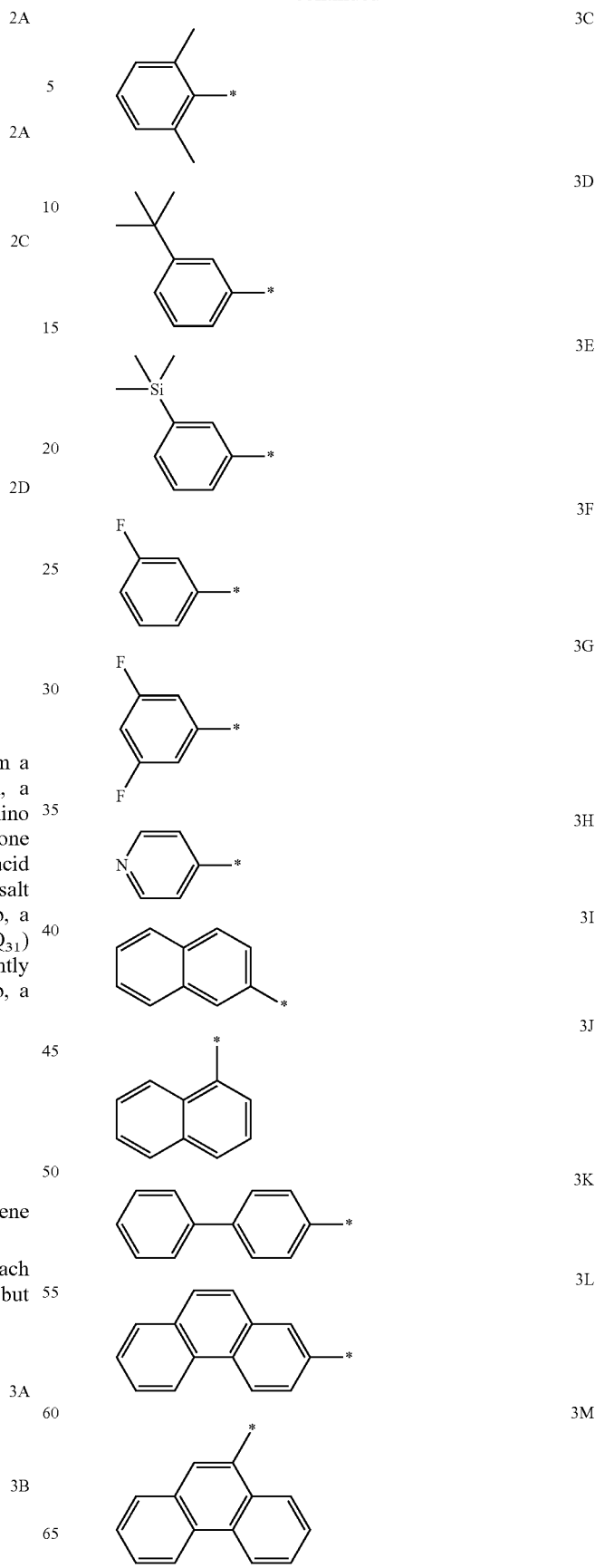

3C

3D

3E

3F

3G

3H

3I

3J

3K

3L

3M

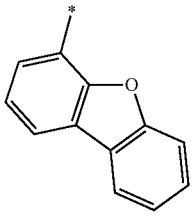
3N

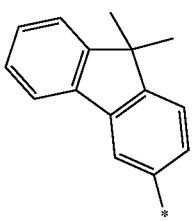
3O

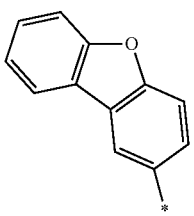
3P

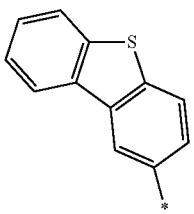
3Q

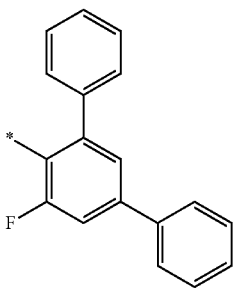
3R $R_1$ and $R_2$ may be each independently selected from:

a methyl group, an ethyl group, a propyl group, a butyl group, a pentyl group, a hexyl group, a heptyl group, an octyl group, a nonyl group, a decyl group, a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group;

a methyl group, an ethyl group, a propyl group, a butyl group, a pentyl group, a hexyl group, a heptyl group, an octyl group, a nonyl group, and a decyl group, each substituted with at least one of a deuterium atom, a halogen atom, a hydroxyl group, a cyano group, a nitro group, and an amino group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group, each substituted with at least one of a deuterium atom, a halogen atom, a hydroxyl group, a cyano group, a nitro group, an amino group, a carboxyl group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_4$-$C_{30}$ heteroaryl group, a $C_6$-$C_{30}$ aryloxy group, a $C_6$-$C_{30}$ arylthio group, and —Si($Q_{31}$)($Q_{32}$)($Q_{33}$) (where, $Q_{31}$ to $Q_{33}$ are each independently selected from a hydrogen atom, a $C_1$-$C_{10}$ alkyl group, a $C_1$-$C_{10}$ alkoxy group, and a $C_1$-$C_{20}$ aryl group).

For example, in Formula 1, $R_1$ to $R_4$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an antracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, and a dibenzocarbazolyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an antracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, and —Si($Q_{31}$)($Q_{32}$)($Q_{33}$) (where, $Q_{31}$ to $Q_{33}$ are each independently selected from a hydrogen atom, a $C_1$-$C_{10}$ alkyl, a $C_1$-$C_{10}$ alkoxy, a phenyl group, and a naphthyl group)

For example, $R_1$ and $R_2$ may be each independently selected from Formulae 4A to 4C:

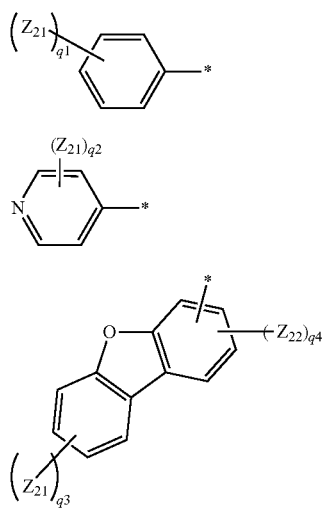

4A

4A

4C

In Formulae 4A to 4C, $Z_{21}$ and $Z_{22}$ may be each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{20}$ aryl group, a $C_4$-$C_{20}$ heteroaryl group, and —Si($Q_{31}$)($Q_{32}$)($Q_{33}$) (where, $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group)

q1 may be an integer selected from 1 to 5;

q2 may be an integer selected from 1 to 4;

q3 may be an integer selected from 1 to 4;

q4 may be an integer selected from 1 to 3; and

* is a binding site.

For example, in Formula 1, $R_1$ and $R_2$ may be each independently selected from an ethyl group, a tert-butyl group, and Formulae 5A to 5D, but are not limited thereto:

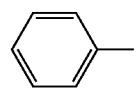

5A

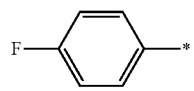

5B

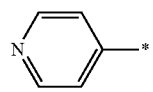

5C

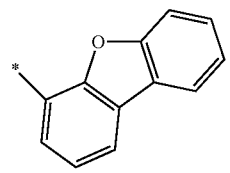

5D

In Formula 1, $R_3$ to $R_6$ may be each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an antracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, and —Si($Q_1$)($Q_2$)($Q_3$) (where, $Q_1$ to $Q_3$ are each independently selected from a hydrogen atom, a $C_1$-$C_{10}$ alkyl group, a $C_1$-$C_{10}$ alkoxy group, and a $C_6$-$C_{20}$ aryl group).

In one embodiment, the condensed cyclic compound represented by Formula 1 may be represented by Formula 1A:

Formula 1A

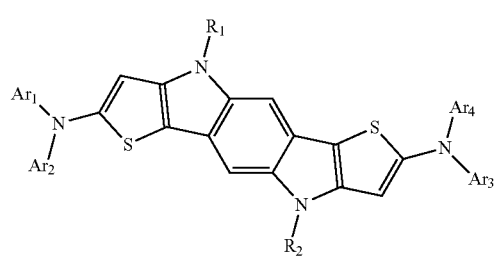

In Formula 1A, descriptions of $Ar_1$ to $Ar_4$, $R_1$, and $R_2$ are the same as defined above.

For example, in Formula 1A, $Ar_1$ to $Ar_4$ may be each independently represented by one of Formulae 2A to 2D, and $R_1$ and $R_2$ may be each independently represented by one of an ethyl group, a butyl group, and Formulae 4A to 4C.

For example, in Formula 1A, $Ar_1$ to $Ar_4$ may be each independently represented by one of Formulae 3A to 3R, and $R_1$ and $R_2$ may be each independently represented by one of an ethyl group, a tert-butyl group, and Formulae 5A to 5D.

The condensed cyclic compound may be represented by one of Compounds 1 to 53:

1

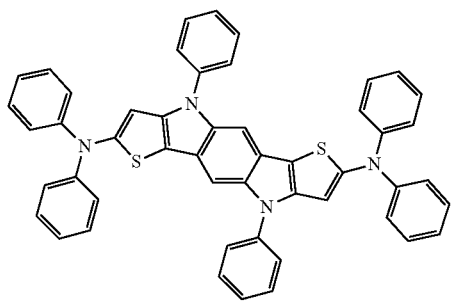

2

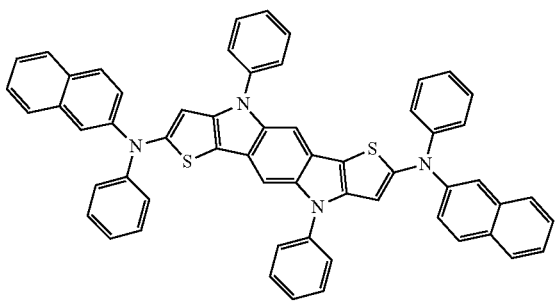

3

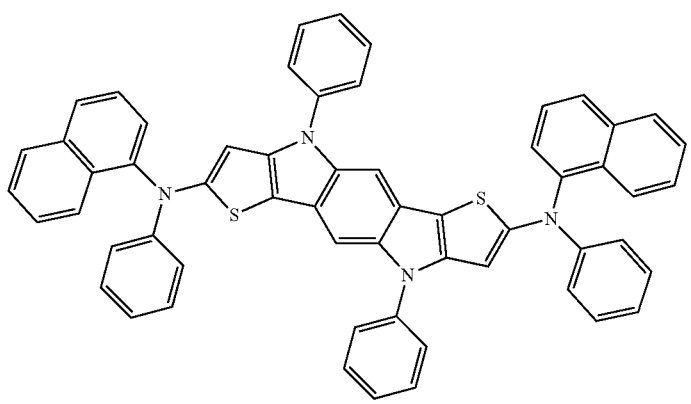

4

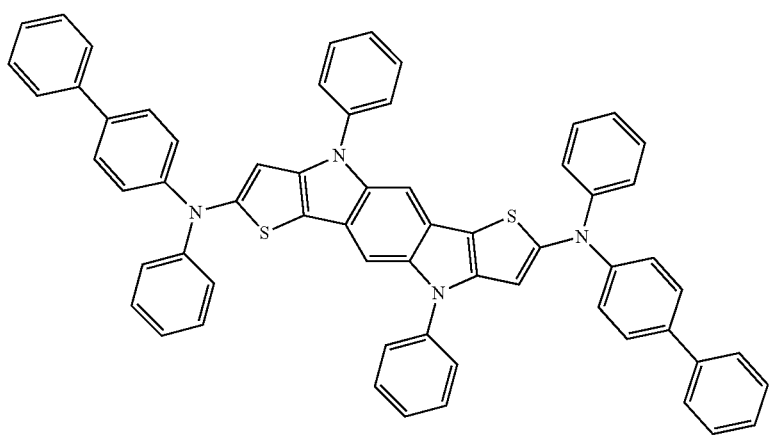

-continued
5
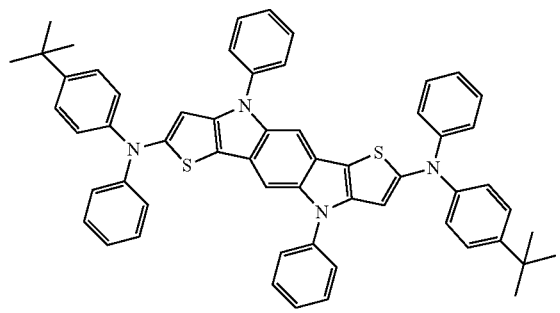
6
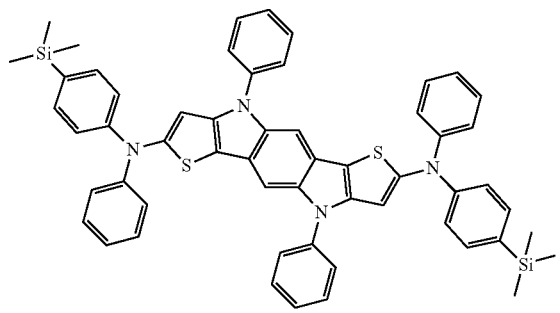
7
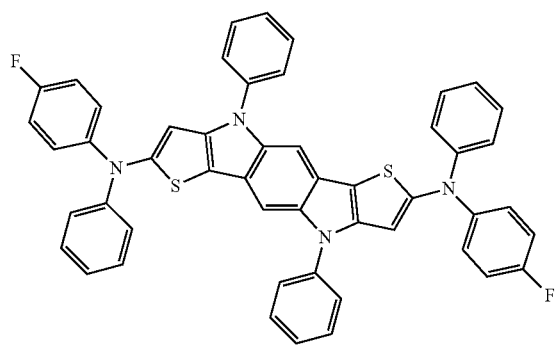
8
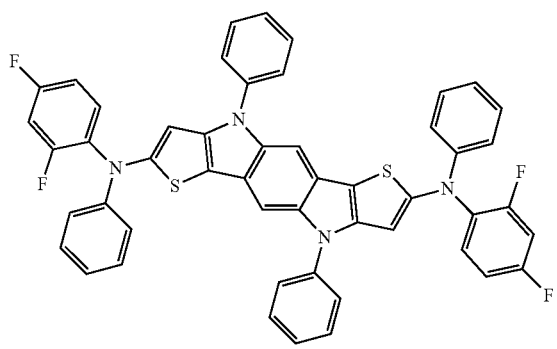
9
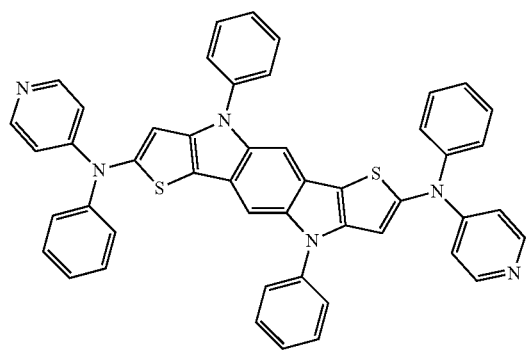
10
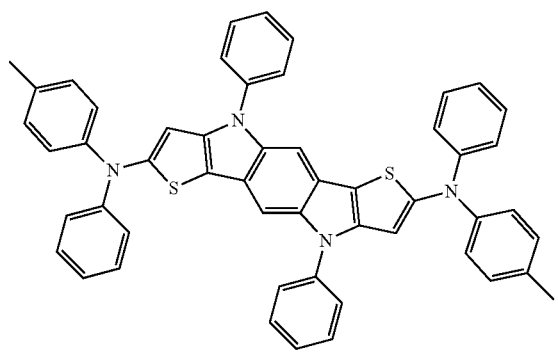
11
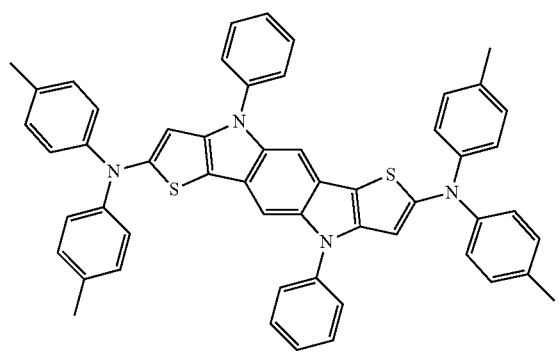
12
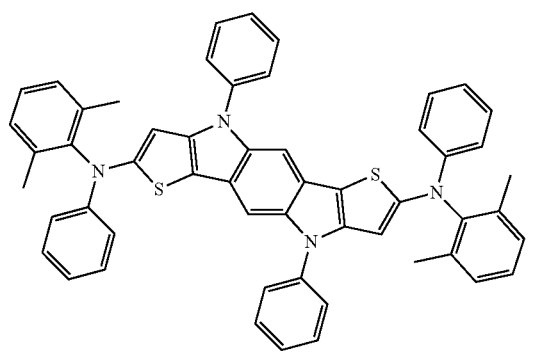

-continued
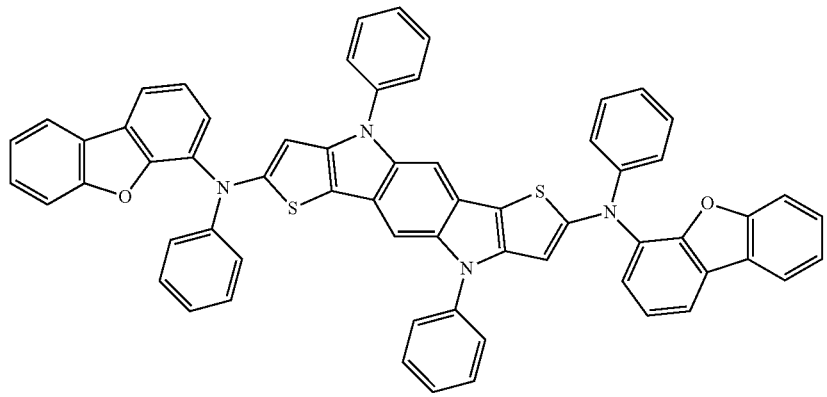
13
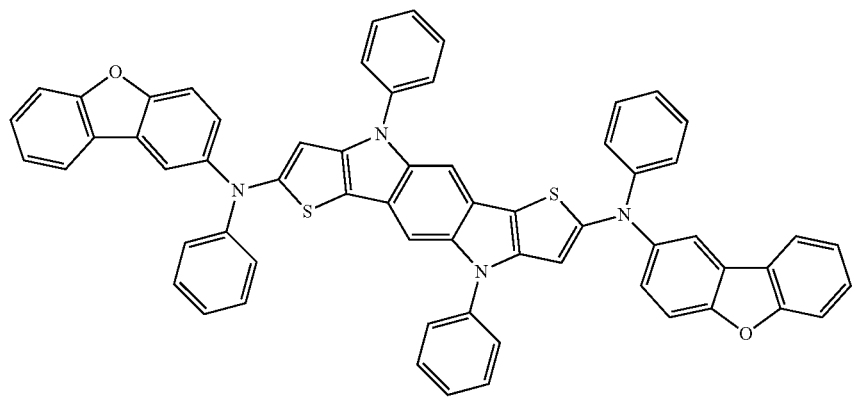
14
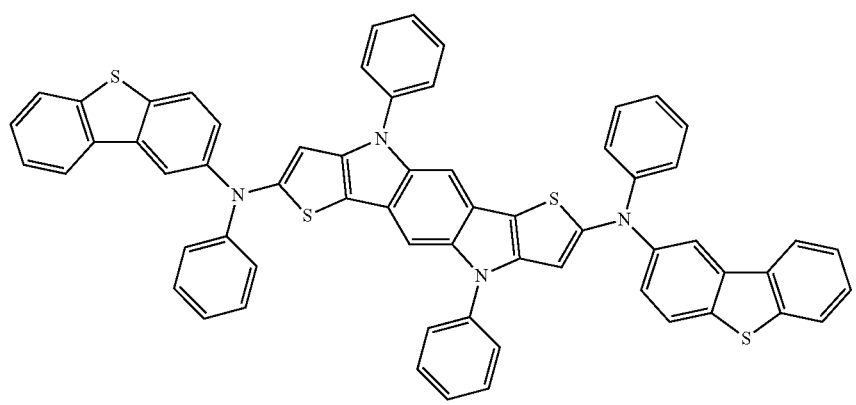
15
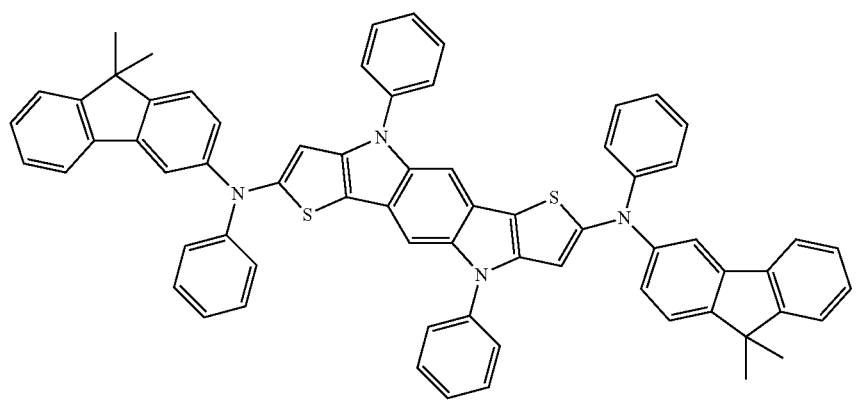
16

-continued
17
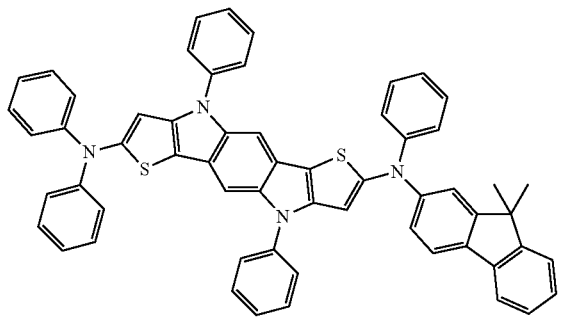
18
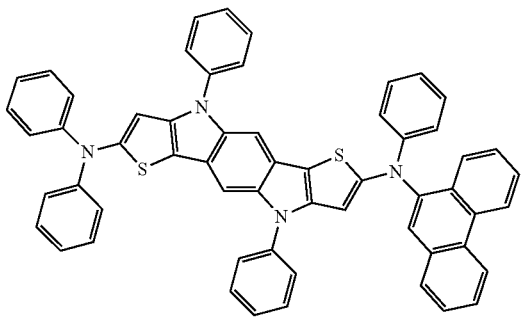
19
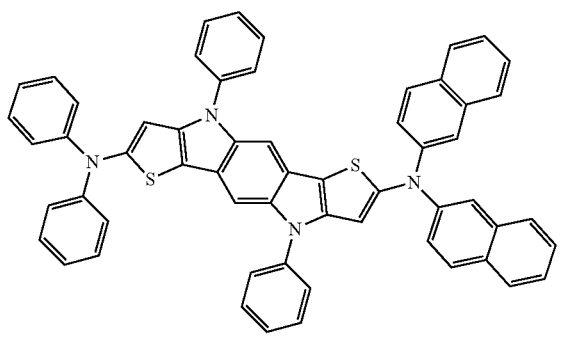
20
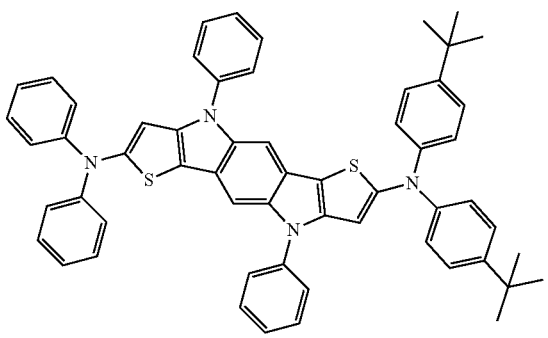
21
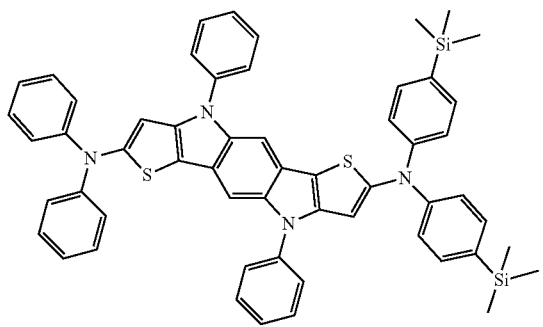
22
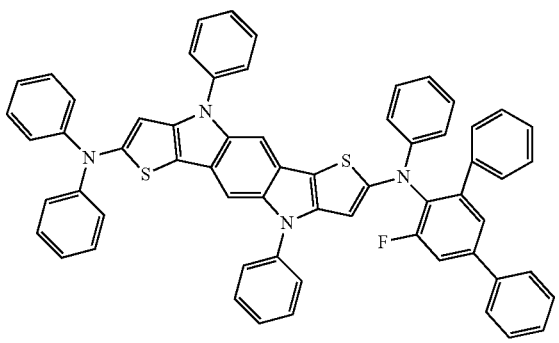
23
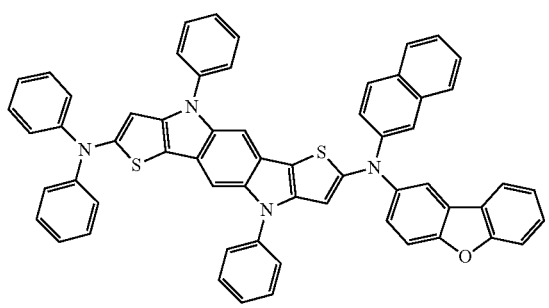
24
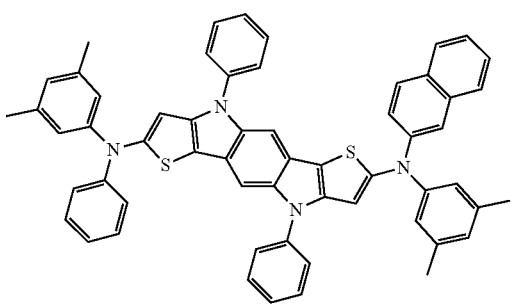

25
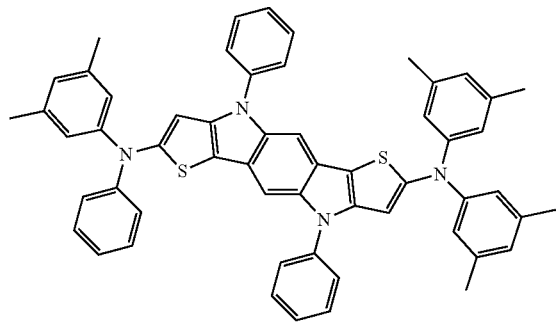
26
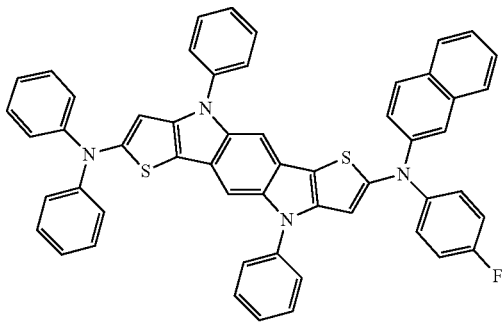
27
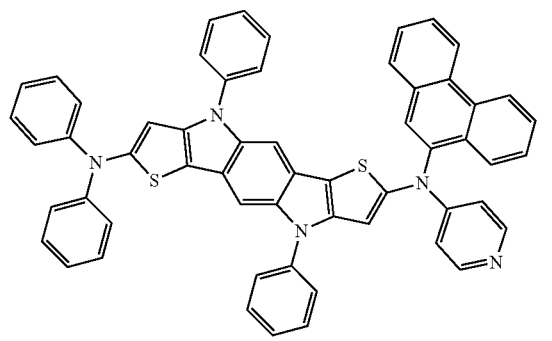
28
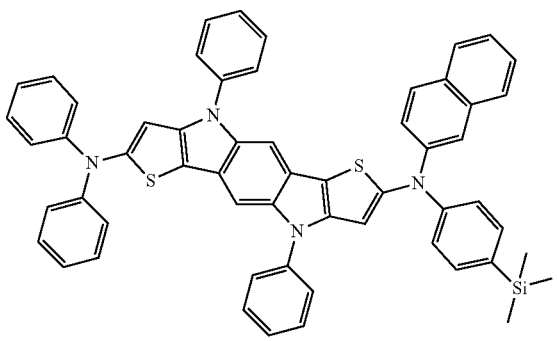
29
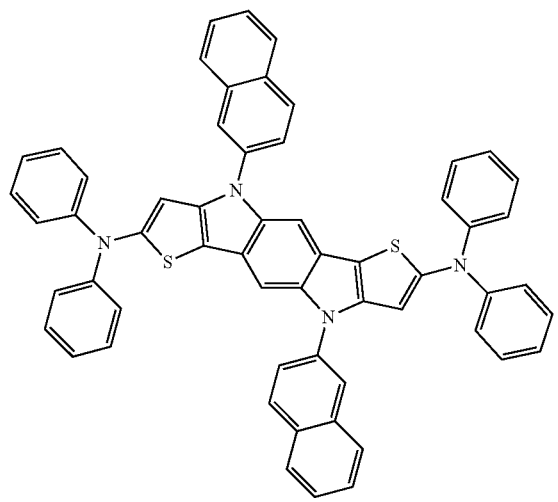
30
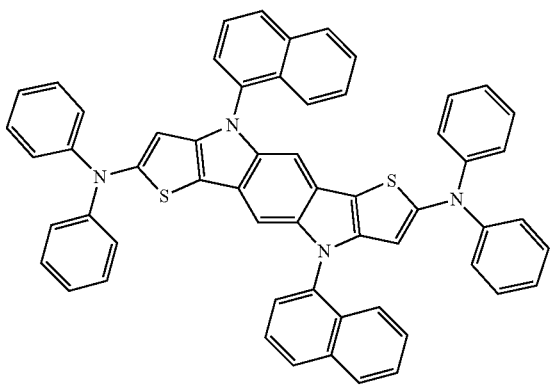

31
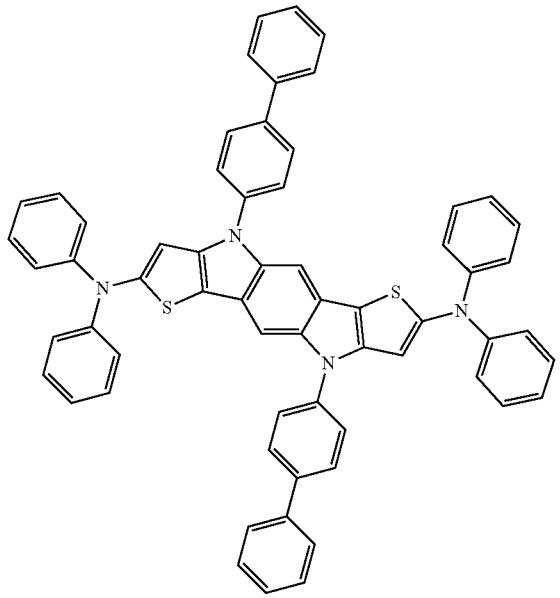
32
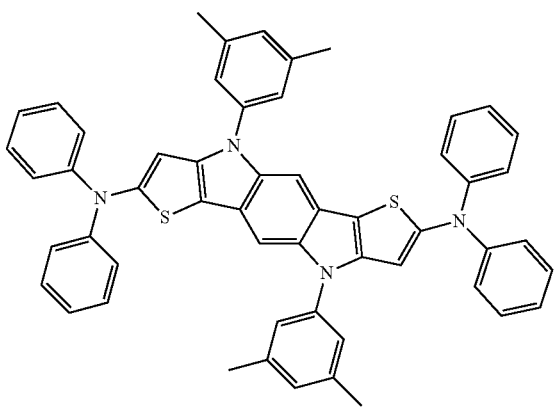
33
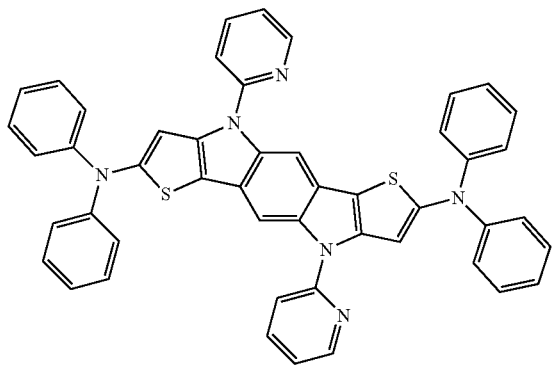
34
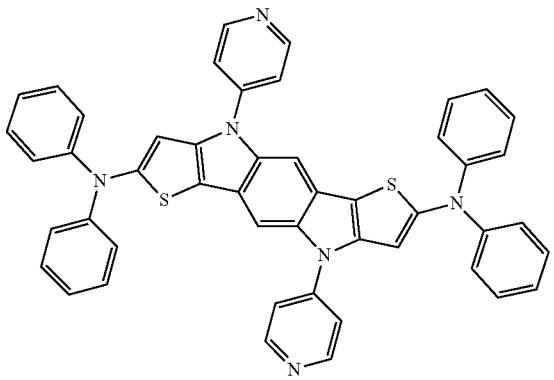
35
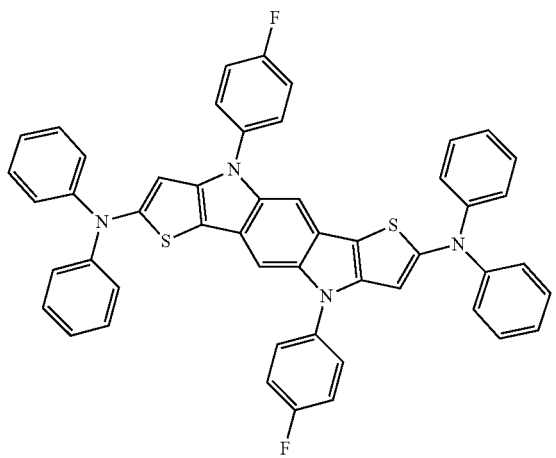
36
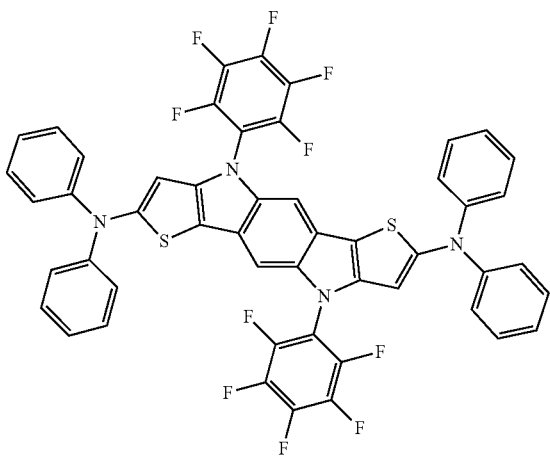

-continued
| 37 | 38 |
|---|---|
| 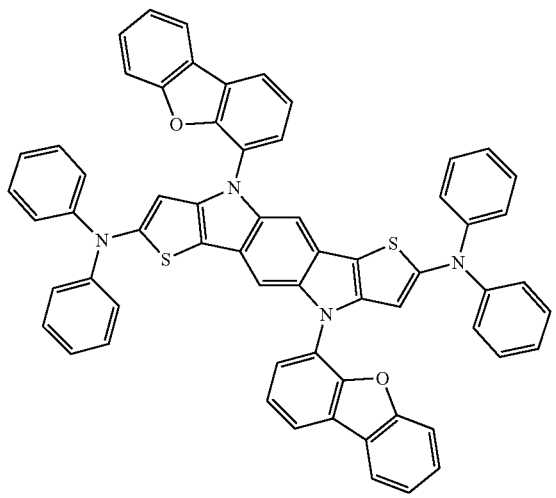 | 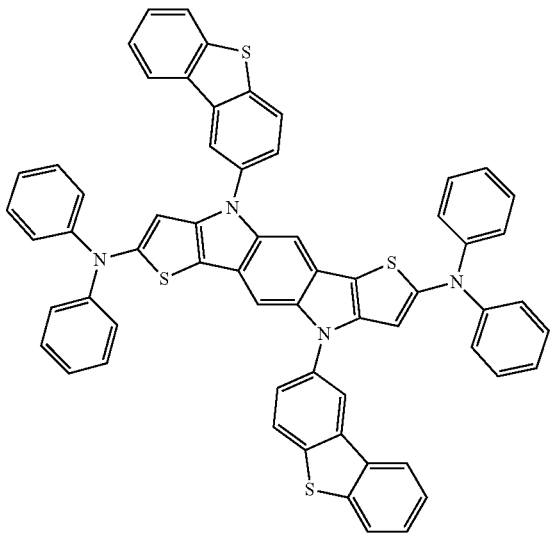 |
| 39 | 40 |
| 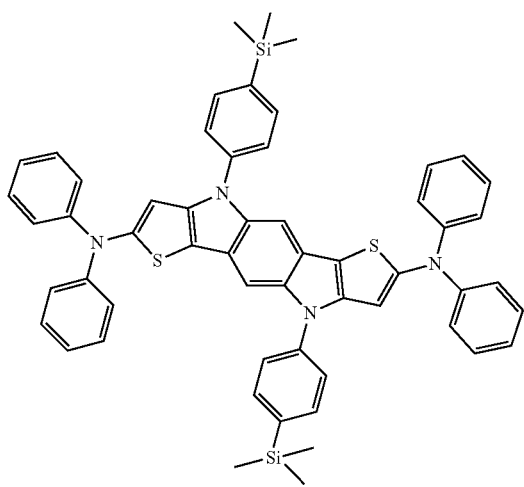 | 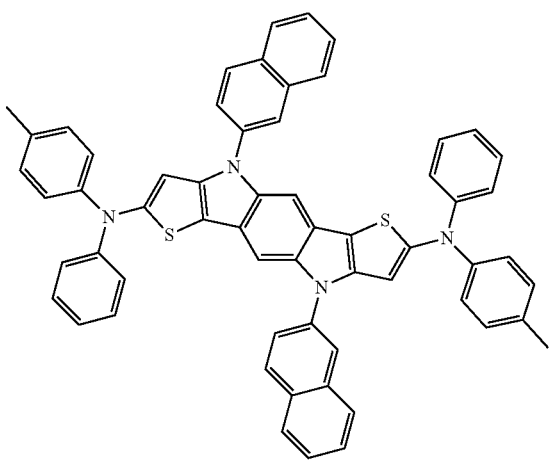 |
| 41 | 42 |
| 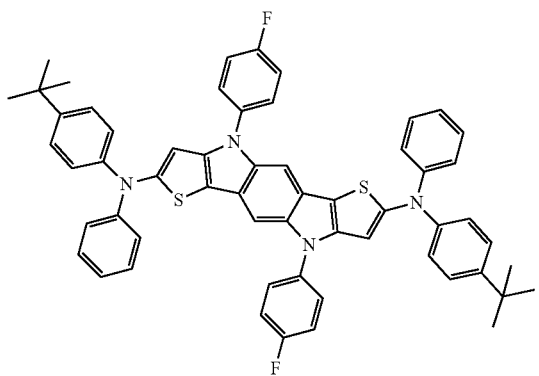 | 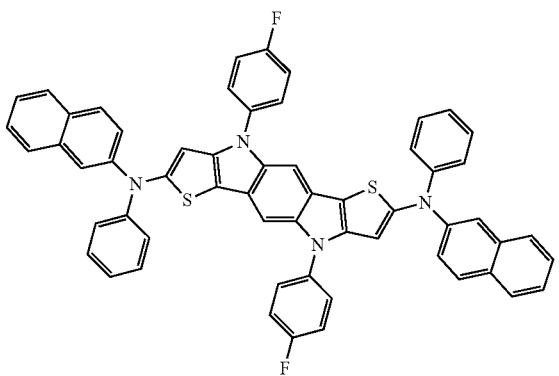 |

-continued
43
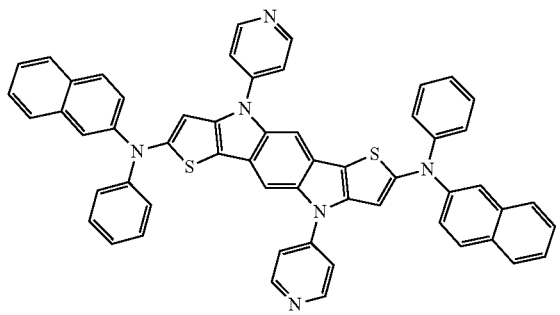
44
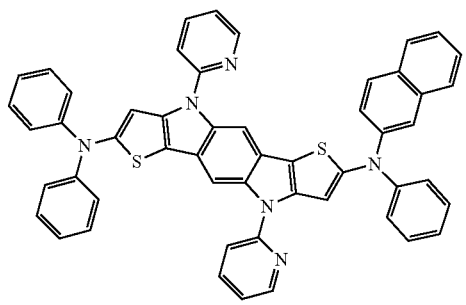
45
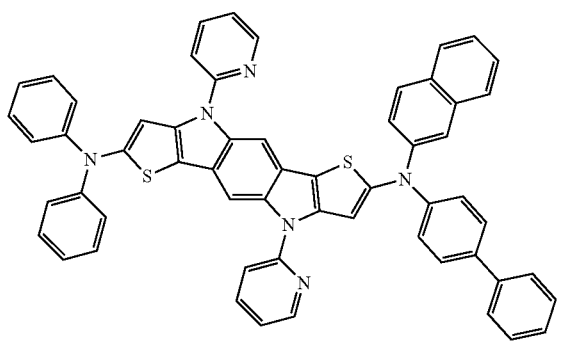
46
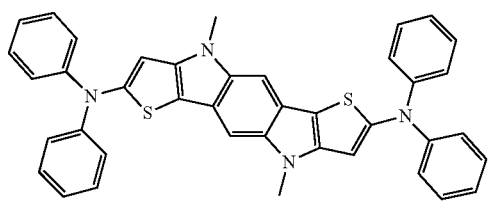
47
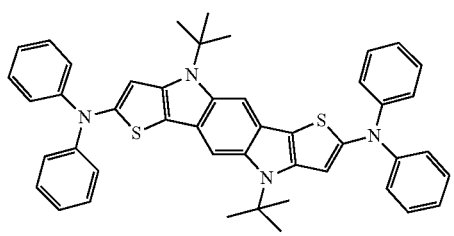
48
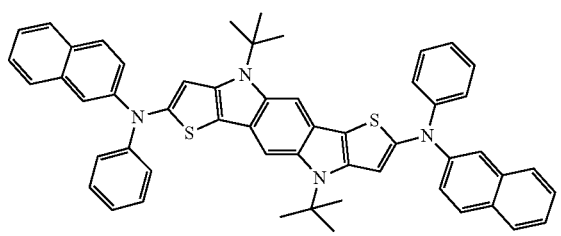
49
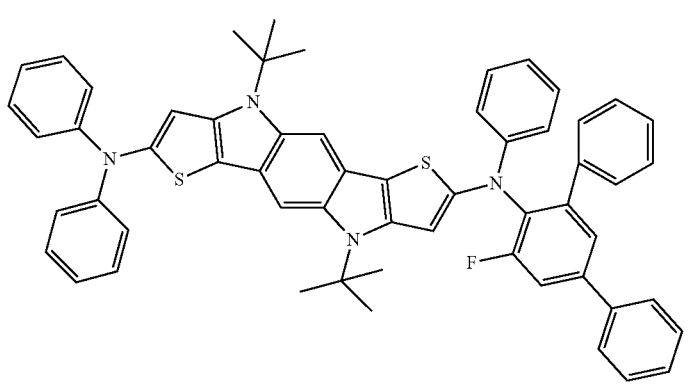

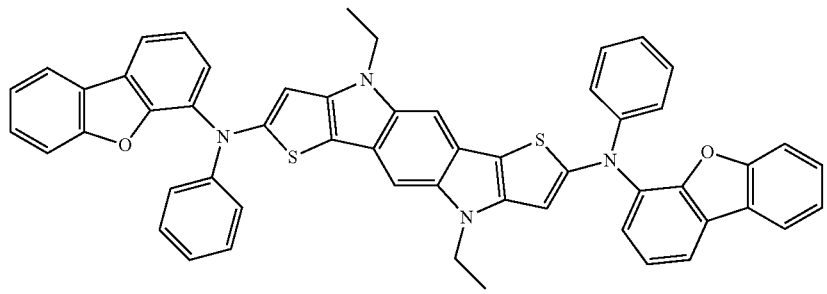
50
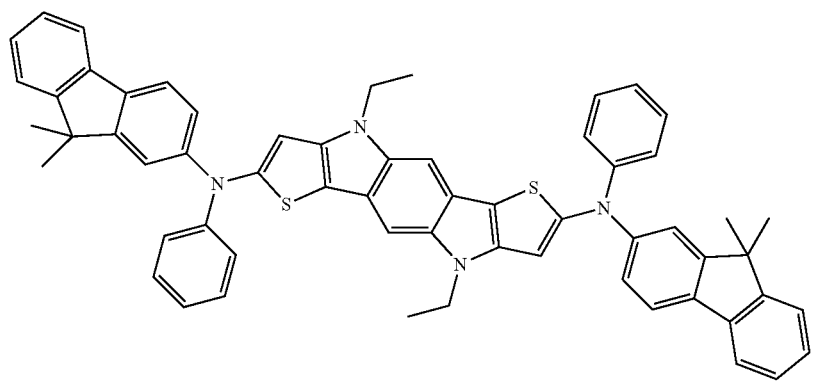
51
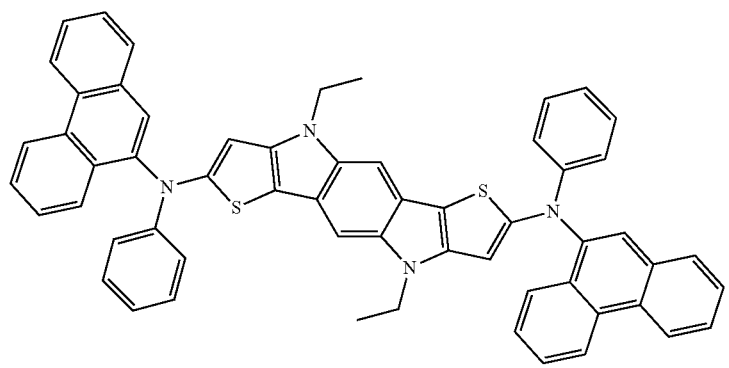
52

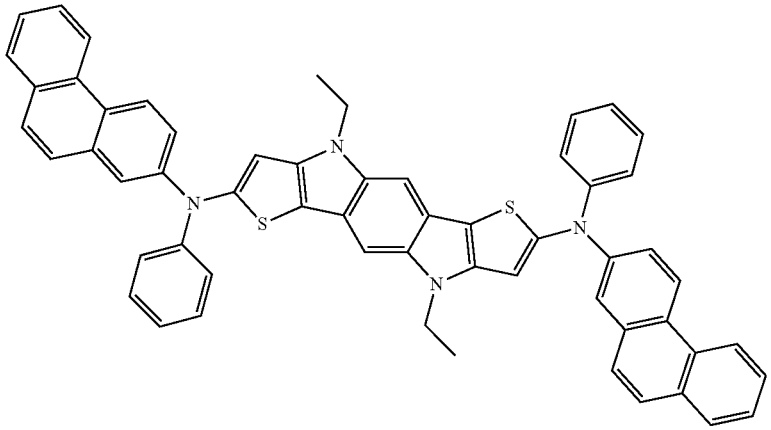

53

The compound represented by Formula 1 may have abundant π-electrons since 14 π-electrons that are delocalized by having a condensed structure of benzene and pyrrole, and unshared electron pairs of sulfur (S) may provide additional electrons to the structure. In this regard, possibilities of π→π* transition and n→π* transition may increase, and thus, a light-emitting efficiency may be increased. Therefore, an organic light-emitting diode (OLED) including the condensed cyclic compound represented by Formula 1 may have a low driving voltage, a high efficiency, a high brightness, and/or a long lifespan.

The condensed cyclic compound represented by Formula 1 may be synthesized by using (utilizing) a known organic synthesis method. The synthesis method of the condensed cyclic compounds may be understood by those of ordinary skill in the art from the examples that will be described below.

The condensed cyclic compound represented by Formula 1 may be included between a pair of electrodes of an OLED. For example, the condensed cyclic compound may be included in a hole transport region, e.g., a hole transport layer (HTL). Thus, provided is an OLED including a first electrode, a second electrode disposed opposite to the first electrode, and an organic layer that is disposed between the first electrode and the second electrode and includes an emission layer (EML), wherein the organic layer includes at least one condensed cyclic compound represented by Formula 1 as described above.

As used herein, the term "(organic layer) includes at least one condensed cyclic compound" may be interpreted as "(organic layer) includes one condensed cyclic compound that is represented by Formula 1 or at least two different condensed cyclic compounds that are each represented by Formula 1 respectively".

For example, the organic layer may include only Compound 1 as the condensed cyclic compound. Here, Compound 1 may be included in the HTL of the OLED. Alternatively, the organic layer may include Compound 1 and Compound 2 as the condensed cyclic compound. Here, Compound 1 and Compound 2 may be included in the same layer (e.g., Compound 1 and Compound 2 may be both included in the HTL) or in different layers (e.g., Compound 1 may be included in the EML, and Compound 2 may be included in the HTL).

The organic layer may further include a hole transport region between the first electrode and the EML; and an electron transport region between the EML and the second electrode. The electron transport region may include at least one of a hole blocking layer (HBL), an electron transport layer (ETL), and an electron injection layer (EIL). The hole transport region may include at least one of an electron blocking layer (EBL), a hole transport layer (HTL), and a hole injection layer (HIL).

The hole transport region may include the condensed cyclic compound represented by Formula 1. For example, the hole transport region may include the HTL, and the HTL may include the condensed cyclic compound represented by Formula 1.

As used herein, the term "organic layer" denotes a single layer and/or multiple layers disposed between the first electrode and the second electrode of the OLED. A material included in a layer of the "organic layer" is not limited to an organic material.

The drawing schematically illustrates a cross-sectional view of an OLED 10 according to an embodiment of the present invention. The OLED 10 includes a substrate 11, a first electrode 13, an organic layer 15, and a second electrode 17.

Hereinafter, a structure and a manufacturing method of the OLED 10 according to an embodiment of the present invention will be described by referring to the drawing.

The substrate 11 may be a glass substrate or a transparent plastic substrate having excellent transparency, surface smoothness, ease of handling, and/or waterproofness.

The first electrode 13 may be formed by providing a first electrode material on a top of the substrate 11 by using (utilizing) a deposition method or a sputtering method. When the first electrode 13 is an anode, the first electrode material may be selected from materials having a high work function to ease hole injection. The first electrode 13 may be a reflective electrode, a semi-transparent electrode, or a transparent electrode. Examples of the first electrode material may be indium tin oxide (ITO), indium zinc oxide (IZO), tin oxide ($SnO_2$), and zinc oxide (ZnO), which are transparent and have excellent conductivity. Also, in order to form the first electrode 13, which is a semi-transparent electrode or a semi-reflective electrode, at least one selected from magnesium (Mg), aluminum (Al), aluminum-lithium (Al—Li), calcium (Ca), magnesium-indium (Mg—In), and magnesium-silver (Mg—Ag) may be used (utilized) as the first electrode material.

The first electrode 13 may have a single layer or a multi-layer structure including multiple layers. For example, the first electrode 13 may have a 3-layers structure of ITO/Ag/ITO, but is not limited thereto.

The organic layer 15 is disposed on the first electrode 13. The organic layer 15 includes an EML.

The organic layer 15 may further include a hole transport region that is disposed between the first electrode and the EML, and an electron transport region that is disposed between the EML and the second electrode.

The hole transport region may include at least one of an HIL, an HTL, a buffer layer, and an EBL; and the electron transport region may include at least one of an HBL, an ETL, and an EIL, but the hole transport region and the electron transport region are not limited thereto.

The hole transport region may have a single layer formed of a single material, a single layer formed of multiple different materials, or multiple layers formed of multiple different materials.

For example, the hole transport region may have a structure of a single layer formed of multiple different materials; or a structure of HIL/HTL, HIL/HTL/buffer layer, HIL/buffer layer, HTL/buffer layer, or HIL/HTL/EBL sequentially stacked on the first electrode 13, but the structure is not limited thereto.

When the hole transport region includes an HIL, the HIL may be formed on the first electrode 13 by using (utilizing) various suitable methods, such as a vacuum deposition method, a spin-coating method, a cast method, a Langmuir-Blodgett (LB) method, an inkjet printing method, a laser printing method, or a laser induced thermal imaging (LITI) method.

When the HIL is formed by using (utilizing) a vacuum deposition method, the deposition conditions may include, for example, a deposition temperature selected from about 100° C. to about 500° C., a vacuum degree selected from about $10^{-8}$ to about $10^{-3}$ Torr, and a deposition rate selected from about 0.01 to about 100 Å/sec in consideration of a compound for an HIL to be deposited and a structure of the desired HIL.

When the HIL is formed by using (utilizing) a spin-coating method, the coating conditions may include, a coating speed selected from about 2,000 rpm to about 5,000 rpm, and a heat-treating temperature selected from about 80° C. to about 200° C. in consideration of a compound for an HIL to be deposited and a structure of the desired HIL.

When the hole transport region include an HTL, the HTL may be formed on the first electrode 13 or the HIL by using (utilizing) various suitable methods, such as a vacuum deposition method, a spin-coating method, a cast method, an LB method, an inkjet printing method, a laser printing method, or an LITI method. When the HIL is formed by using (utilizing) a vacuum deposition method or a spin-coating method, the deposition conditions and the coating conditions of the HTL may be referenced or referred to the deposition conditions and the coating conditions of the HIL.

The hole transport region may include at least one of a compound represented by Formula 1, m-MTDATA, TDATA, 2-TNATA, NPB, β-NPB, TPD, spiro-TPD, spiro-NPB, α-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), (polyaniline)/poly(4-styrenesulfonate) (PANT/PSS), a compound represented by Formula 201, and a compound represented by Formula 202:

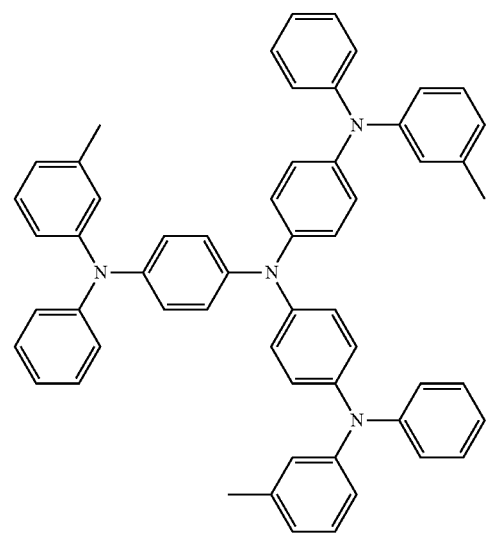

m-MTDATA

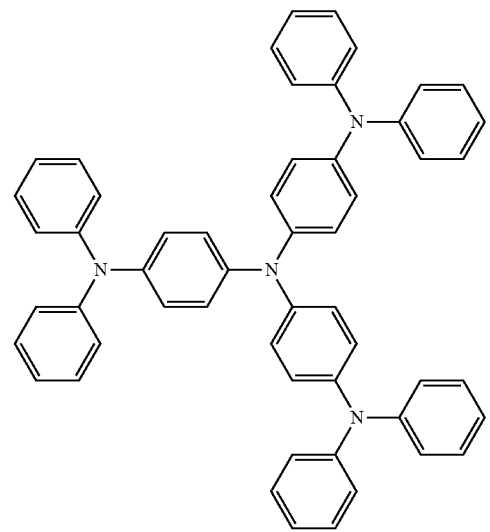

TDATA

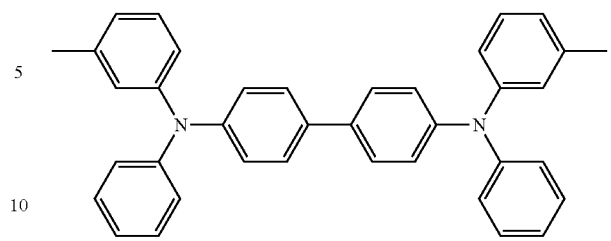
TPD
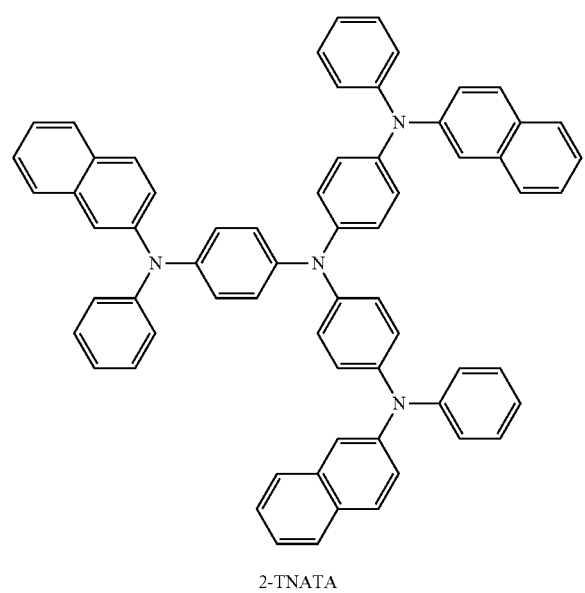
2-TNATA
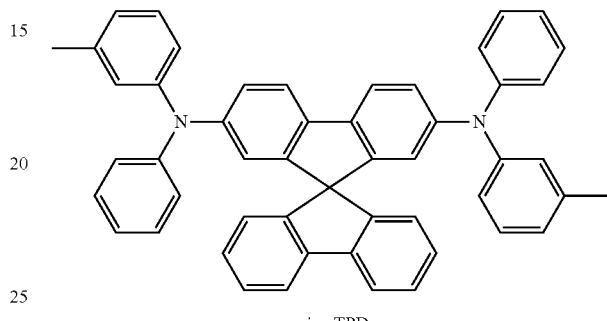
spiro-TPD
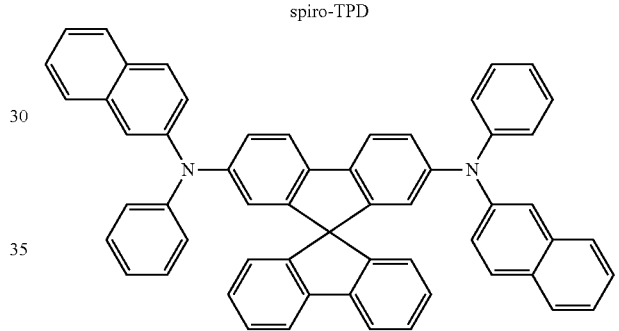
spiro-NPB
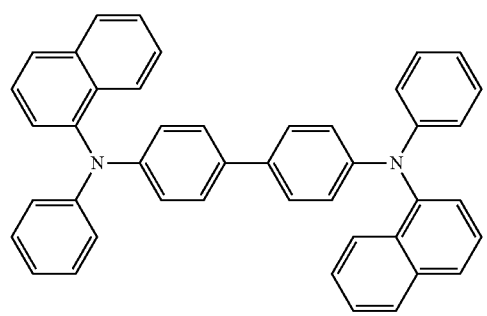
NPB
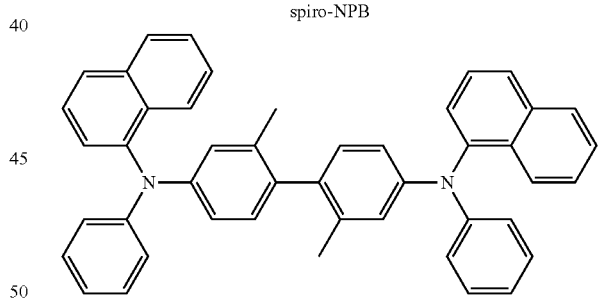
α-NPD
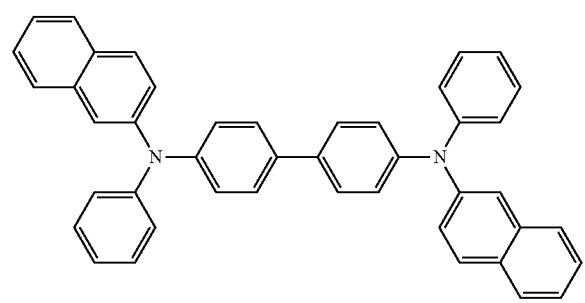
β-NPB
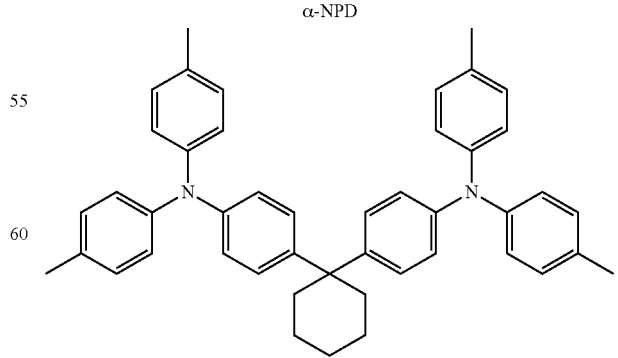
TAPC

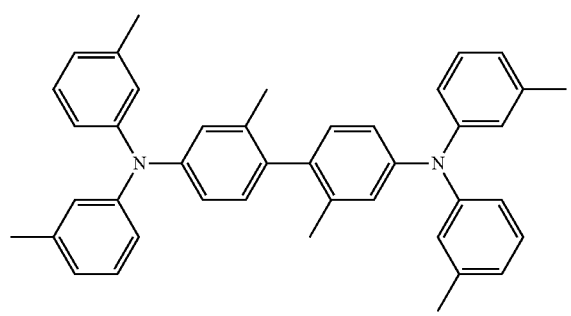

HMTPD

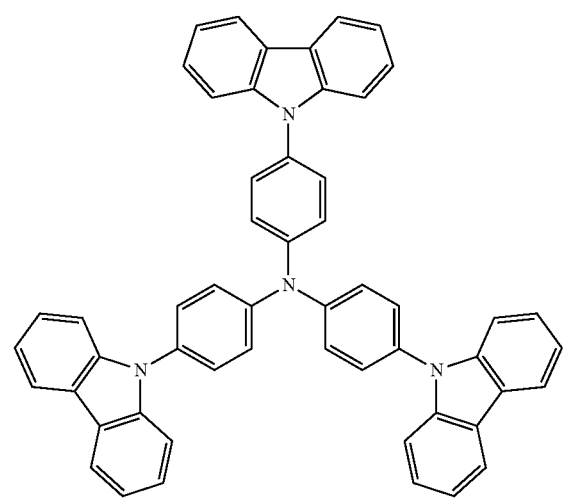

TCTA

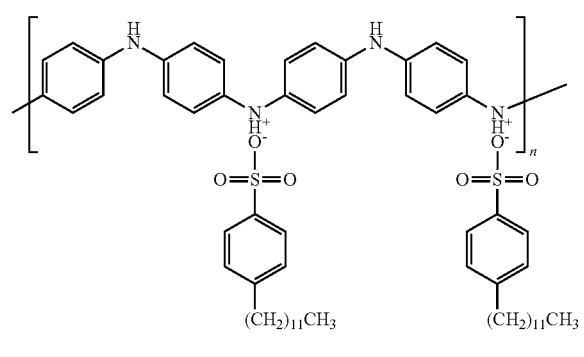

PANI/DBSA

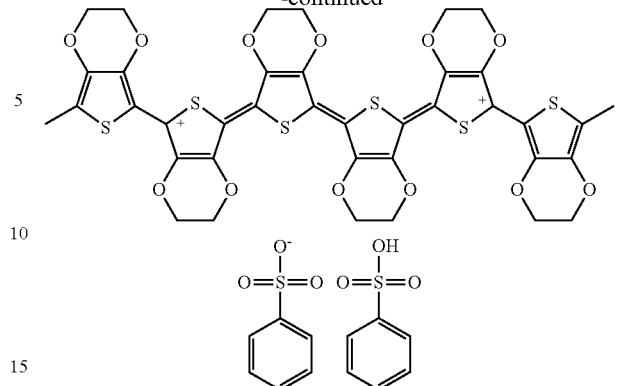

PEDOT/PSS

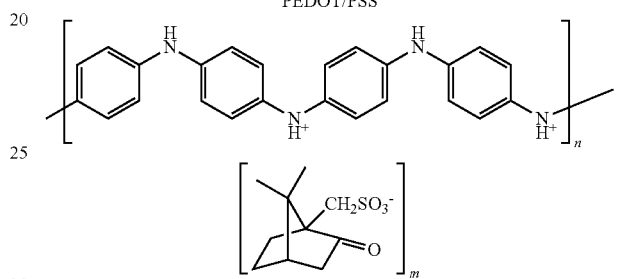

PANI/CSA

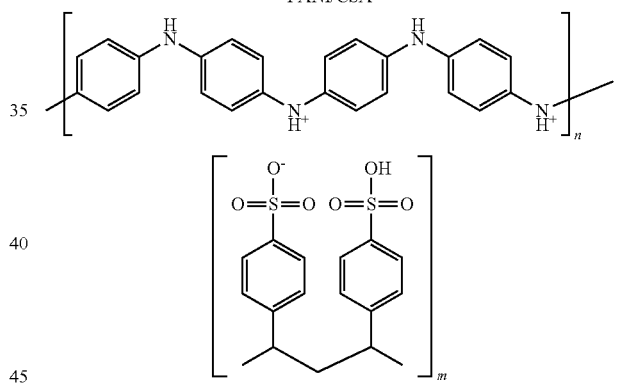

PANI/PSS

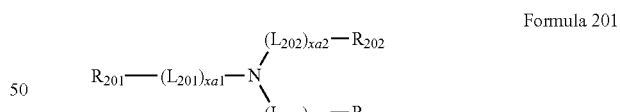

Formula 201

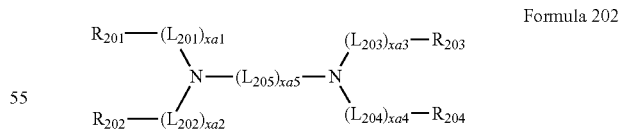

Formula 202

In Formulae 201 and 202, $L_{201}$ to $L_{205}$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, and a substituted or unsubstituted divalent $C_6$-$C_{60}$ non-aromatic condensed polycyclic group;

xa1 to xa4 may be each independently selected from 0, 1, 2 and 3;

xa5 may be selected from 1, 2, 3, 4, and 5; and $R_{201}$ to $R_{205}$ may be each independently selected from a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, and a substituted or unsubstituted monovalent $C_6$-$C_{30}$ non-aromatic condensed polycyclic group.

For example, in Formulae 201 and 202, $L_{201}$ to $L_{205}$ may be each independently selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an antracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{205}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spires-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but are not limited thereto.

For example, the compound represented by Formula 201 may be represented by Formula 201A:

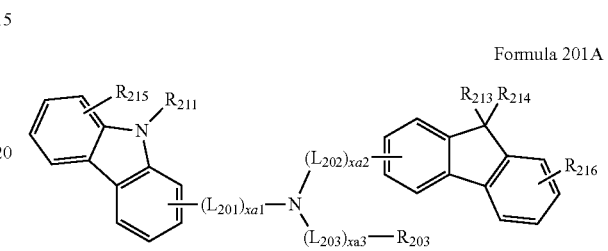

Formula 201A

For example, the compound represented by Formula 201 may be represented by Formula 201A-1, but is not limited thereto:

Formula 201A-1

The compound represented by Formula 202 may be represented by Formula 202A, but is not limited thereto:

Formula 202A

In Formulae 201A, 201A-1, and 202A, the descriptions of $L_{201}$ to $L_{203}$, xa1 to xa3, xa5, $R_{202}$ to $R_{204}$ may be referenced or referred to the descriptions stated in the present specification, the description of $R_{211}$ may be referenced or referred to the description of $R_{203}$, and $R_{213}$ to $R_{216}$ may be each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a $C_6$-$C_{60}$ non-aromatic condensed polycyclic group.

For example, in Formulae 201A, 201A-1 and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an antracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an antracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:

a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof;

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 is 1 or 2.

In Formulae 201A and 201A-1, $R_{213}$ and $R_{214}$ may be combined to each other and form a saturated ring or an unsaturated ring.

The compound represented by Formula 201 and the compound represented by Formula 202 may include Compound HT1 to HT20, but are not limited thereto:

HT1

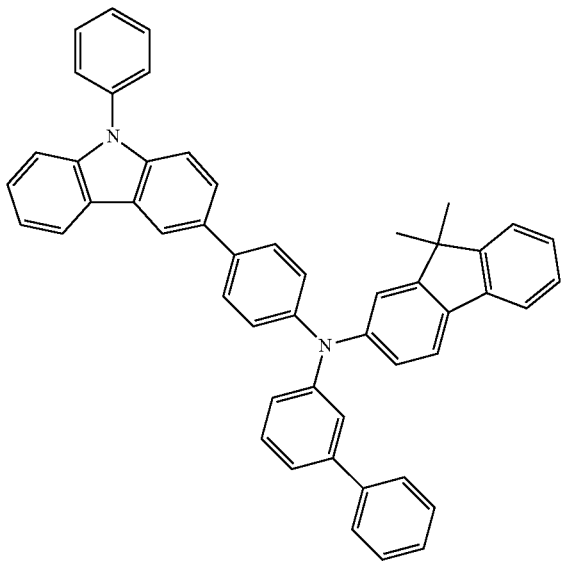

HT2

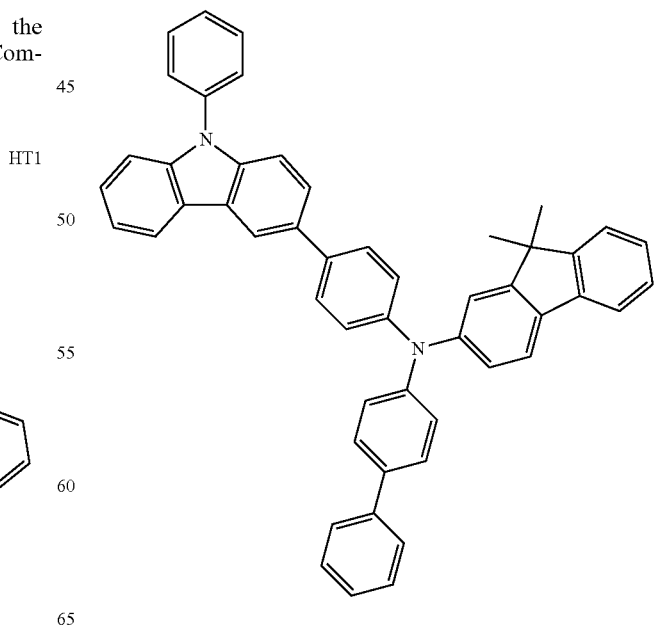

HT3

HT4
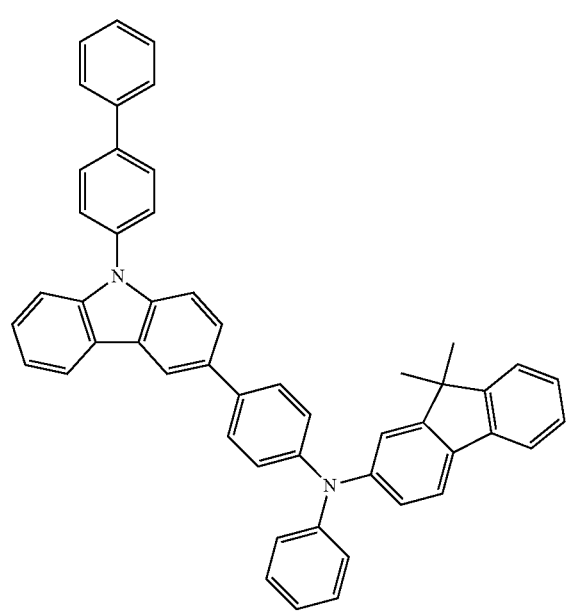
HT5
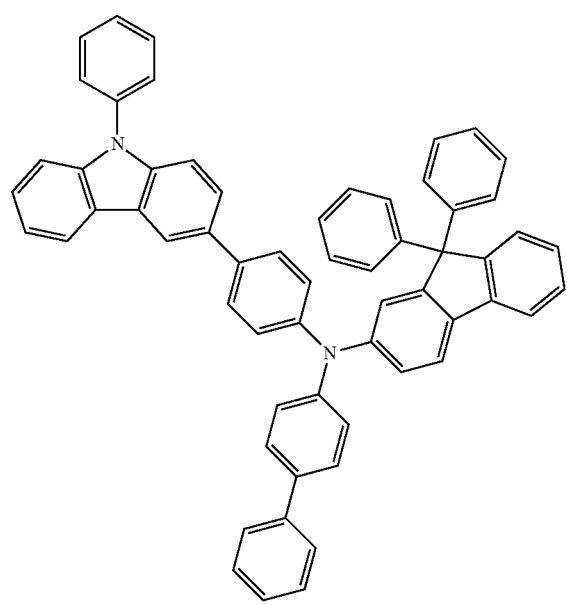
HT6
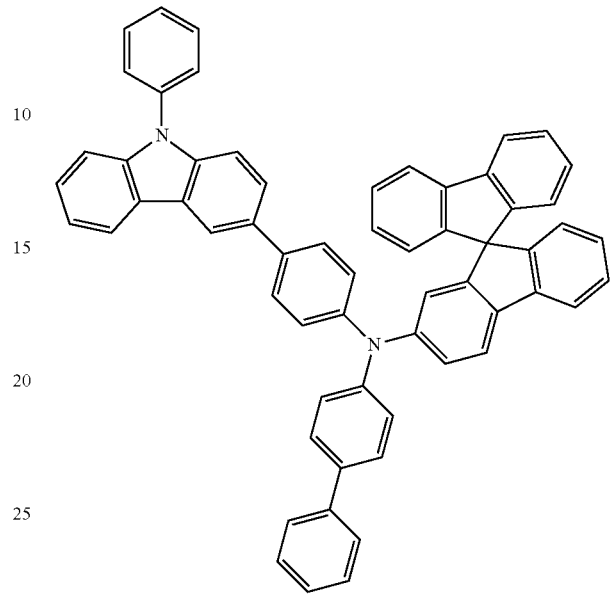
HT7
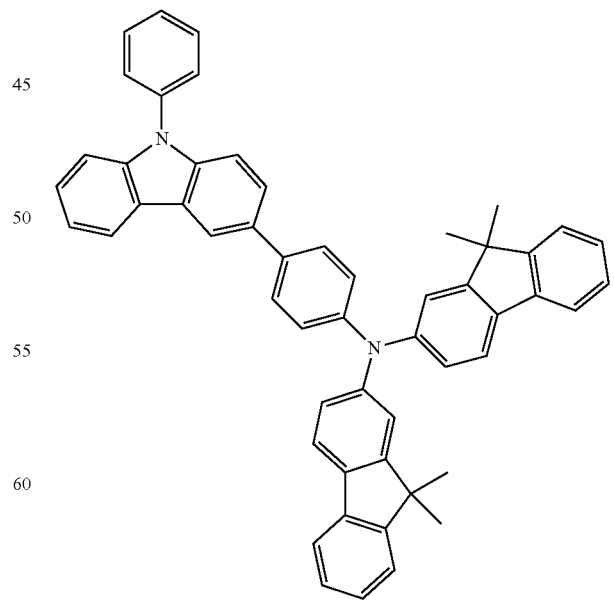

-continued
HT8
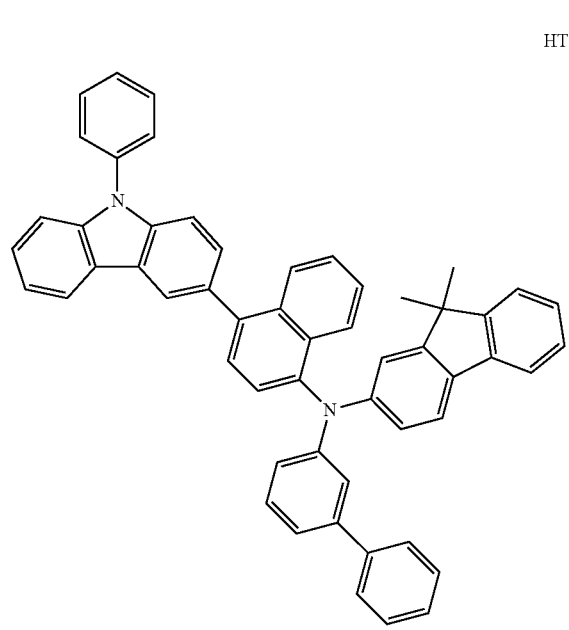
HT10
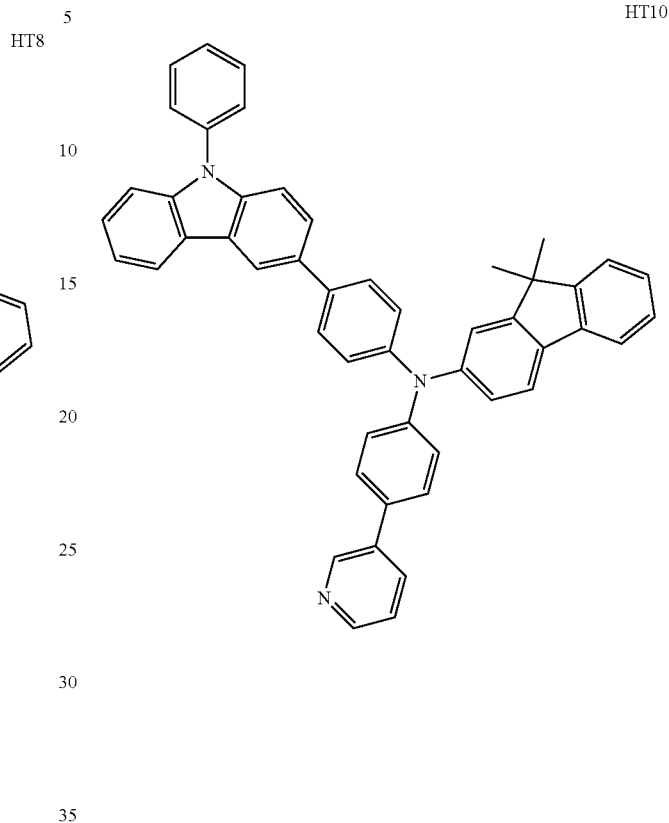
HT9
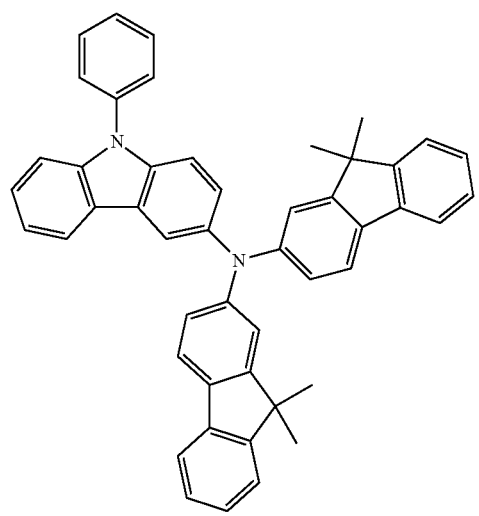
HT11
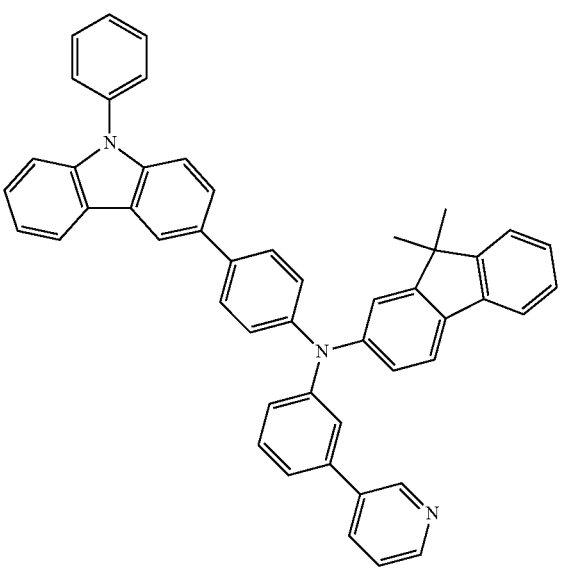

HT12
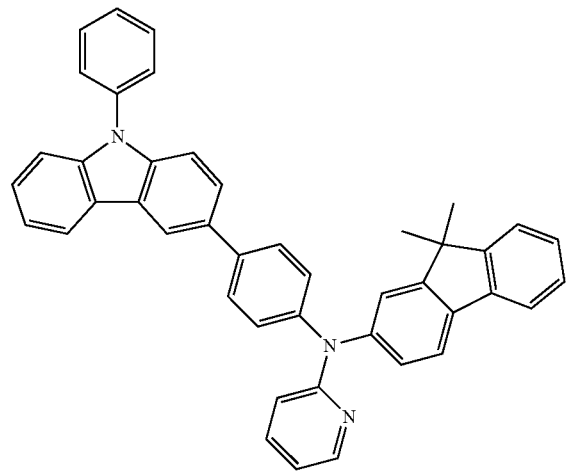
HT13
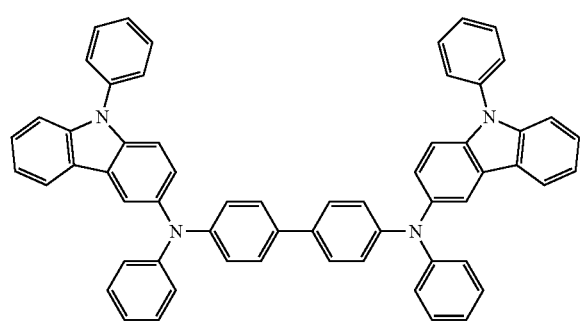
HT14
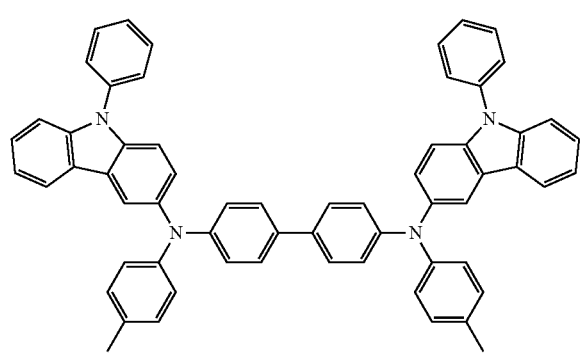
HT15
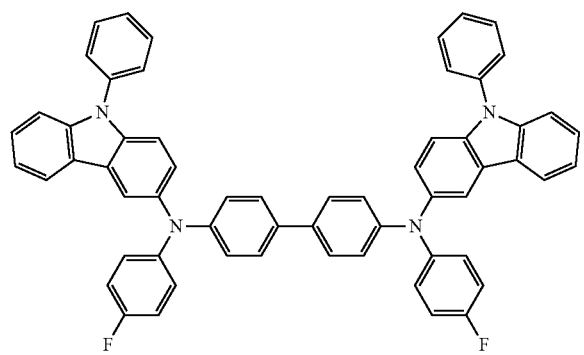
HT16
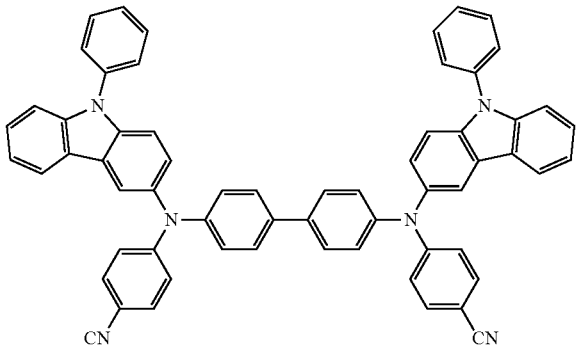
HT17
HT18
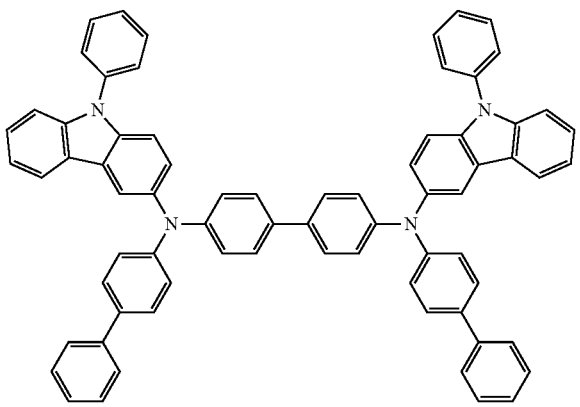
HT19

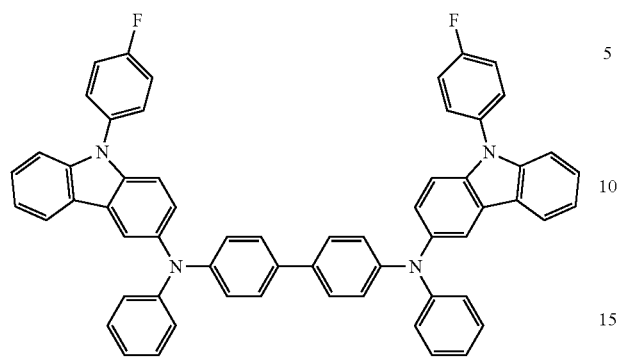

HT20

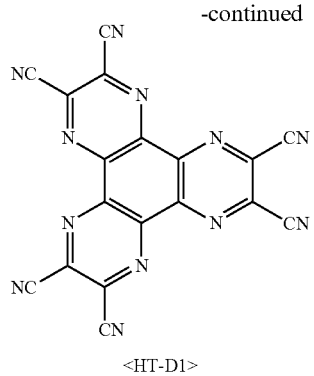

<HT-D1>

A thickness of the hole transport region may be in a range of about 100 Å to about 10,000 Å, for example, about 100 Å to about 1,000 Å. When the hole transport region included both the HIL and the HTL, a thickness of the HIL may be in a range of about 100 Å to about 10,000 Å, for example, about 100 Å to about 1,000 Å; and a thickness of the HTL may be in a range of about 50 Å to about 2,000 Å, for example, about 100 Å to about 1,500 Å. In one embodiment, when thicknesses of the hole transport region, the HIL, and the HTL are within these ranges above, satisfactory hole transport properties are obtained without a substantial increase in driving voltage.

The hole transport region may further include a charge-generating material in addition to the materials described above to improve conductivity. The charge-generating material may be homogeneously or nonhomogeneously distributed in the hole transport region.

The charge-generating material may be, for example, a p-dopant. The p-dopant may be one of a quinone derivative, a metal oxide, and a cyano group-containing compound, but is not limited thereto. Examples of the p-dopant may include, but are not limited to, quinone derivatives (such as tetra-cyanoquinodimethane (TCNQ) or 2,3,5,6-tetrafluoro-tetracyano-1,4-benzoquinodimethane (F4-TCNQ)); metal oxides (such as a tungsten oxide or a molybdenum oxide); and cyano-containing compounds (such as Compound HT-D1 below or the like):

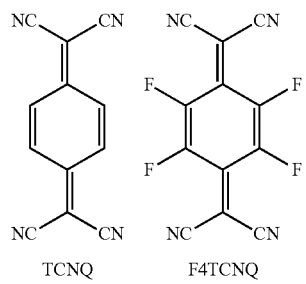

TCNQ  F4TCNQ

The hole transport region may further include at least one of a buffer layer and an EBL in addition to the HIL and the HTL, which are described above. The buffer layer may increase a light-emitting efficiency by compensating an optical resonance distance according to the wavelength of light emitted from the EML. A material included in the buffer layer may be a material that may be included in the hole transport region. The EBL is a layer that blocks electron injection from the electron transport region.

The EML may be formed on the first electrode 13 or the hole transport region by using (utilizing) various suitable methods, such as a vacuum deposition method, a spin-coating method, a cast method, an LB method, an inkjet printing method, a laser printing method, or an LITI method. When the EML is formed by using (utilizing) a vacuum deposition method or a spin-coating method, the deposition conditions and the coating conditions of the EML may be referenced or referred to the deposition conditions and the coating conditions of the HIL.

When the OLED 10 is for a full-color OLED display, the EML may be patterened into a red EML, a green EML, and a blue EML for each subpixel. Alternatively, the EML may have a staked structure of a red EML, a green EML, and a blue EML; or a structure in which a red light-emitting material, a green light-emitting material, and a blue light-emitting material are mixed in one layer, and thus white light may be emitted.

The EML may include a host and a dopant.

The host may include at least one of TPBi, TBADN, ADN (also, referred to as "DNA"), CBP, CDBP and TCP:

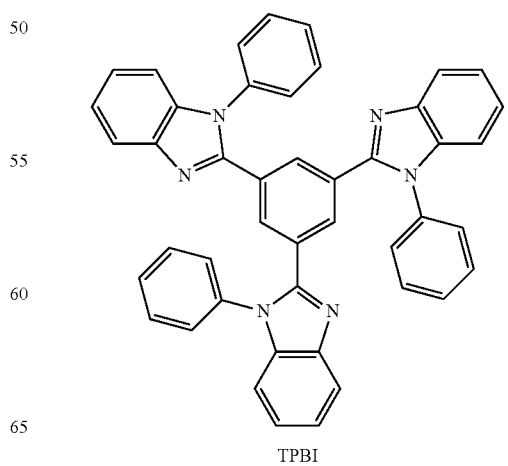

TPBI

-continued

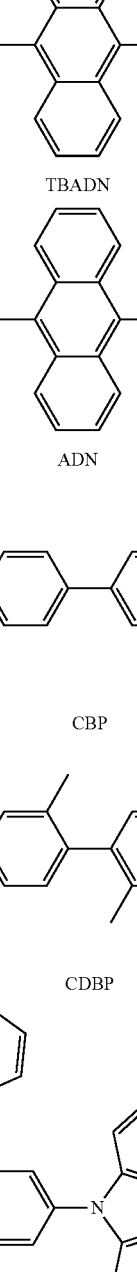

TBADN

ADN

CBP

CDBP

TCP

Also, the host may include a compound represented by Formula 301:

$$Ar_{301}\text{-}[(L_{301})_{xb1}\text{-}R_{301}]_{xb2}$$  Formula 301

In Formula 301, $Ar_{301}$ may be selected from:

naphthalene, hepthalene, fluorenene, spiro-fluorenene, benzofluorenene, dibenzofluorenene, phenalene, phenanthrene, anthracene, fluoranthene, triphenylene, pyrene, chrysene, naphthacene, picene, perylene, pentaphene, and indenoanthracene; and naphthalene, hepthalene, fluorenene, spiro-fluorenene, benzofluorenene, dibenzofluorenene, phenalene, phenanthrene, anthracene, fluoranthene, triphenylene, pyrene, chrysene, naphthacene, picene, perylene, pentaphene, and indenoanthracene, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent $C_2$-$C_{60}$ non-aromatic condensed polycyclic group, and —Si($Q_{301}$)($Q_{302}$)($Q_{303}$) (where, $Q_{301}$ to $Q_{303}$ are each independently selected from a hydrogen atom, a $C_1$-$C_{60}$ alkyl group, a $C_2$-$C_{60}$ alkenyl group, a $C_6$-$C_{60}$ aryl group, and a $C_2$-$C_{60}$ heteroaryl group);

the description of $L_{301}$ may be referenced or referred to the description of $L_{201}$ in the present specification;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is an integer selected from 0, 1, 2, and 3; and xb2 is an integer selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an antracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an antracenylene group, a pyrenylene group, and a chrysenylene group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from:

a $C_1$-$C_{20}$ alkyl and a $C_1$-$C_{20}$ alkoxy;

a $C_1$-$C_{20}$ alkyl and a $C_1$-$C_{20}$ alkoxy, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but are not limited thereto.

For example, the host may include a compound represented by Formula 301A:

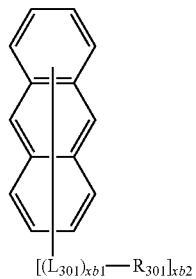

Formula 301A

In Formula 301A, the descriptions of the substituents are as defined in the present specification.

The compound represented by Formula 301 may include at least one of Compound H1 to H42, but is not limited thereto:

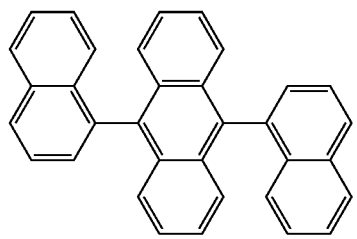

H1

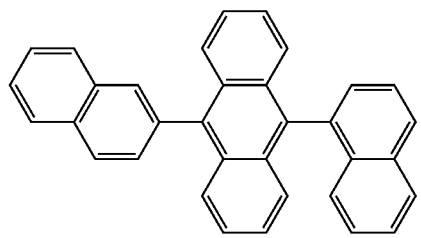

H2

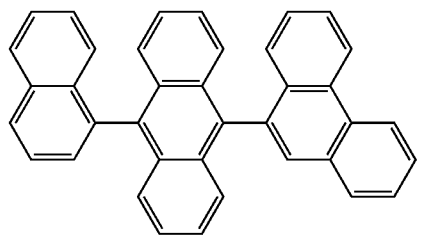

H3

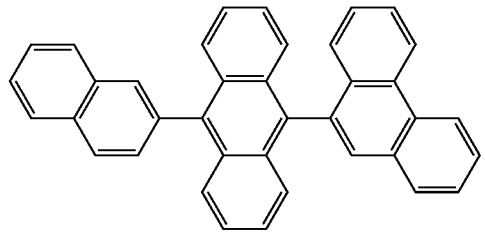

H4

H5
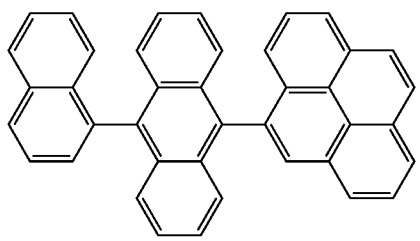
H6
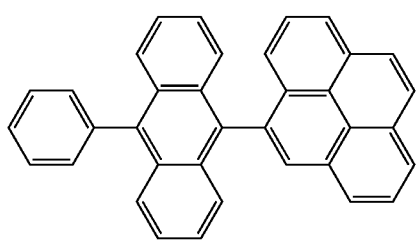
H7
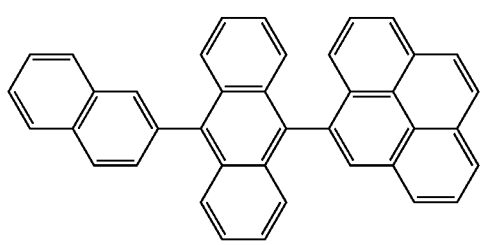
H8
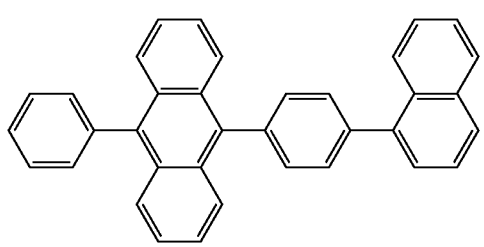
H9
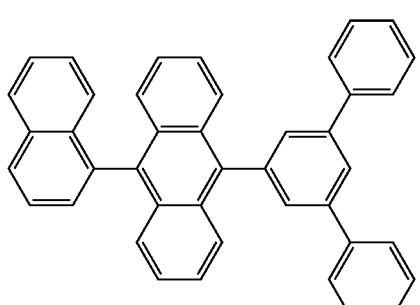
H10
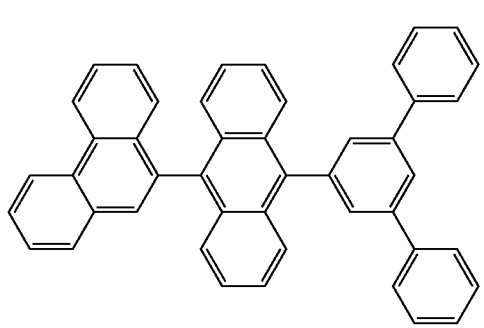
H11
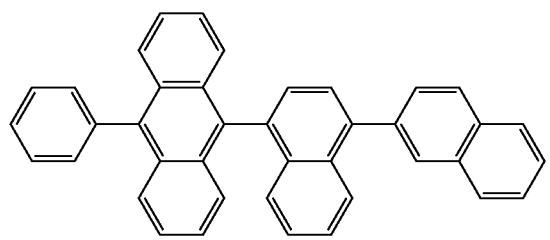
H12
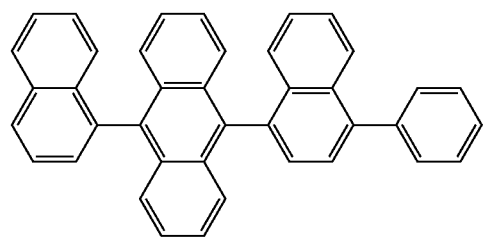
H13
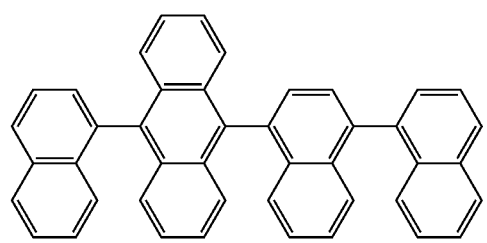
H14
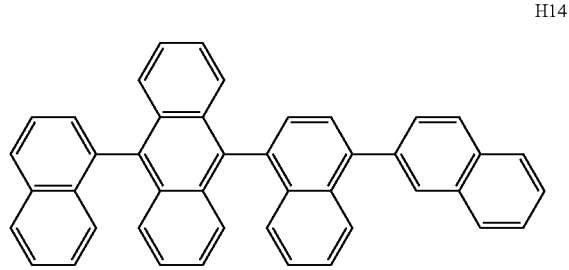
H15
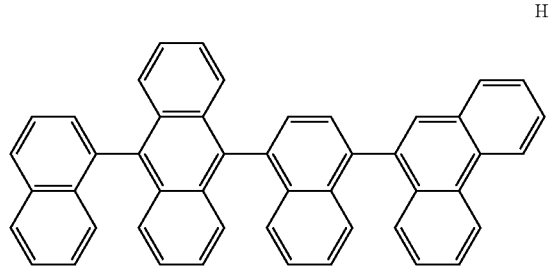
H16
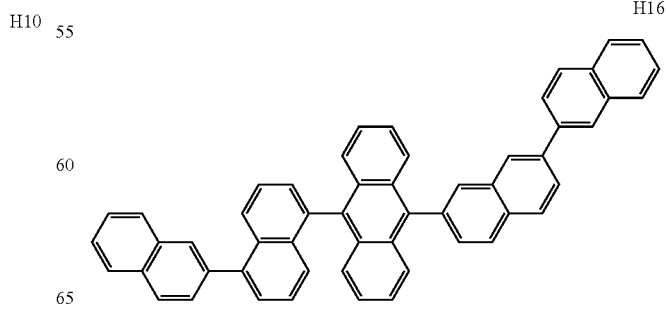

-continued
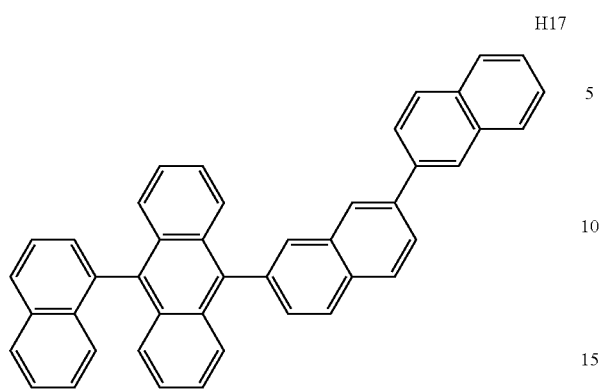
H17
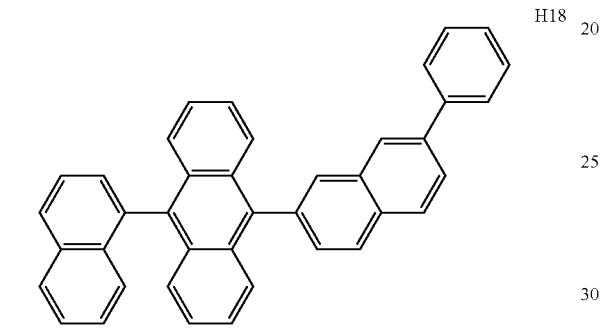
H18
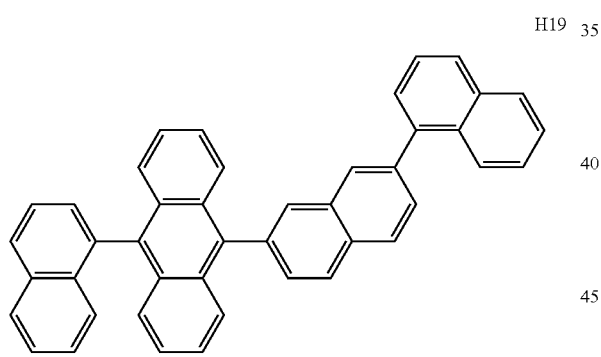
H19
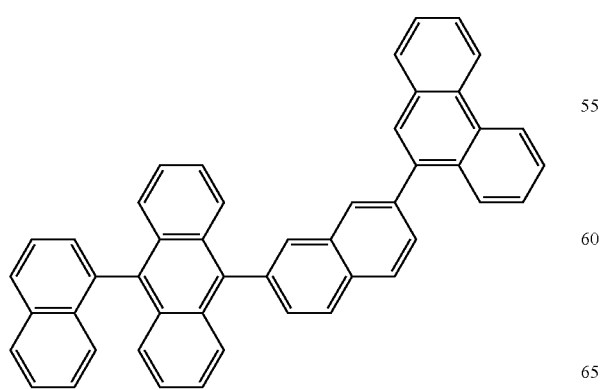
H20
-continued
H21
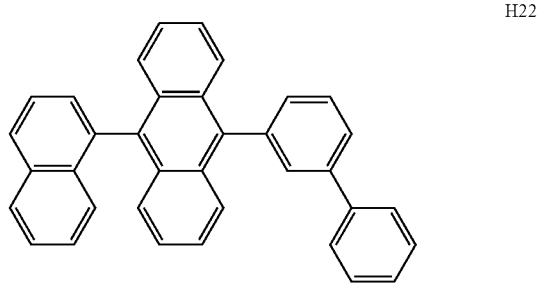
H22
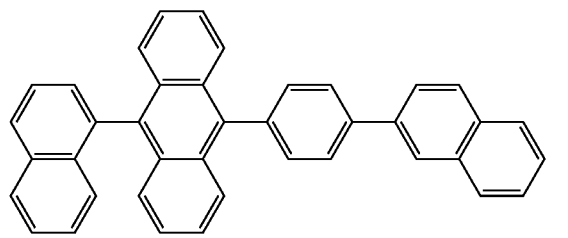
H23
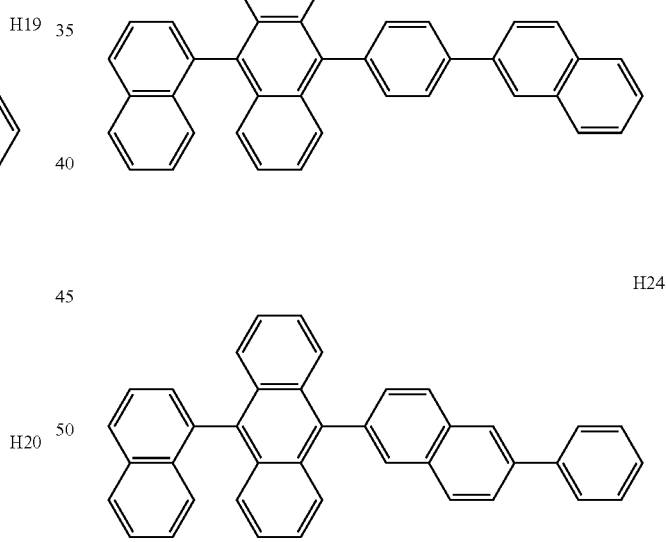
H24
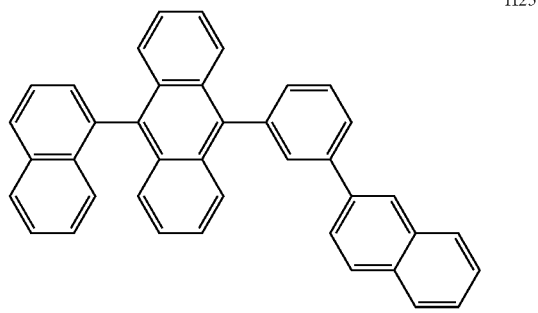
H25

H26
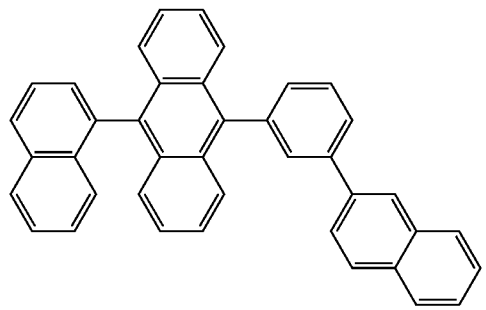
H27
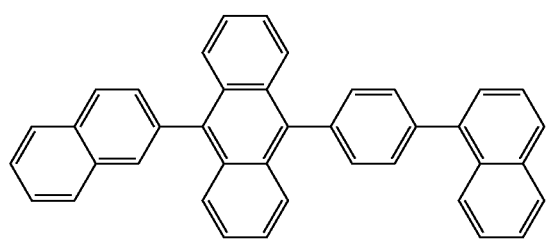
H28
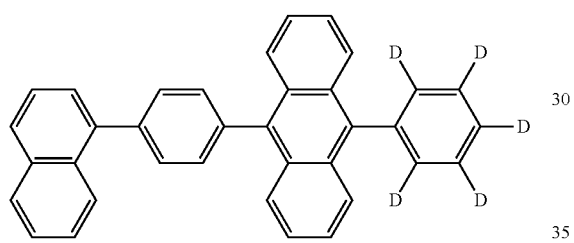
H29
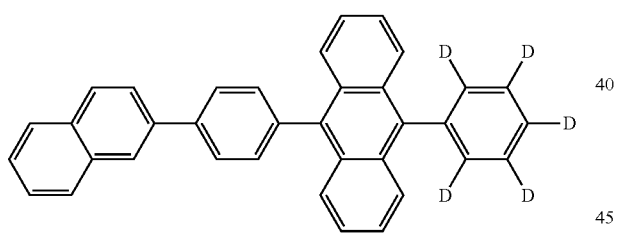
H30
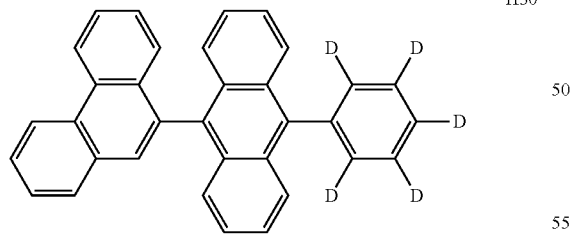
H31
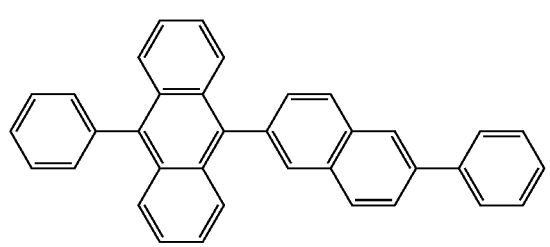
H32
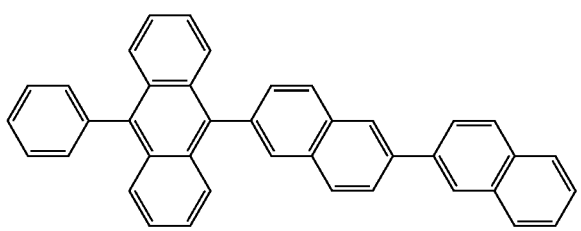
H33
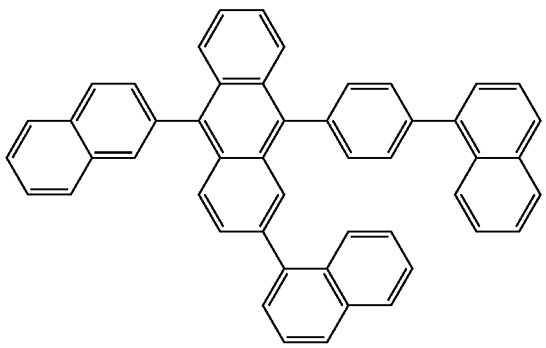
H34
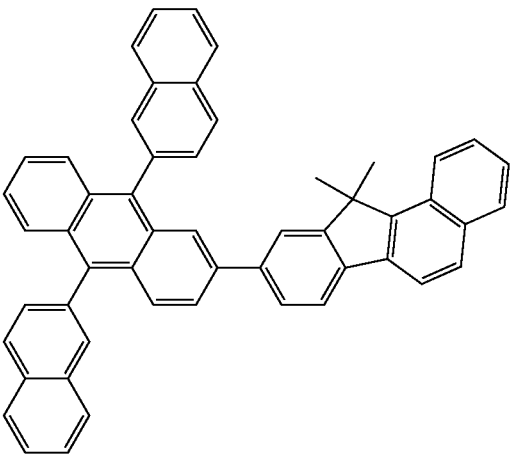
H35
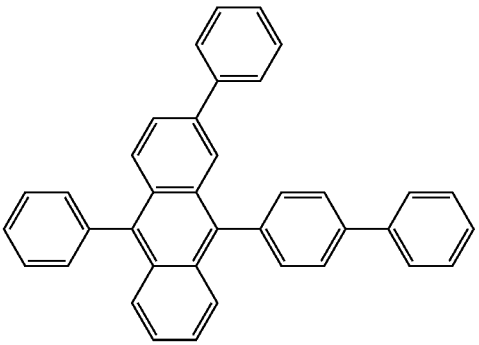

H36
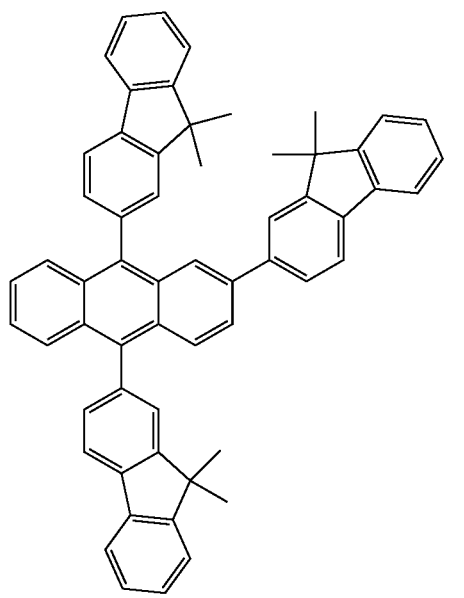
H39
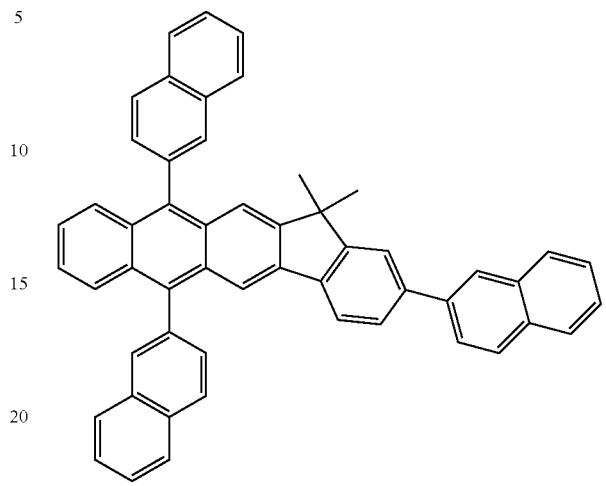
H37
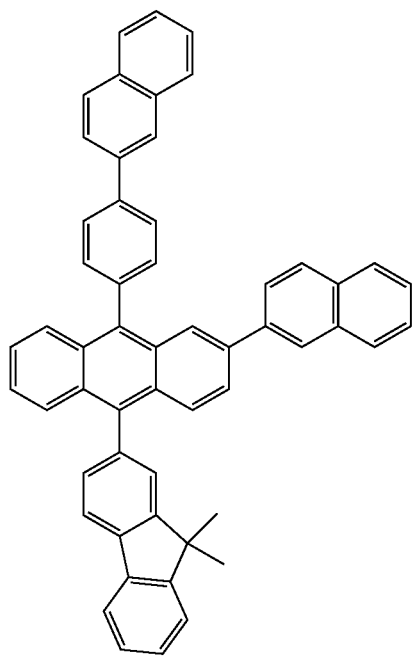
H40
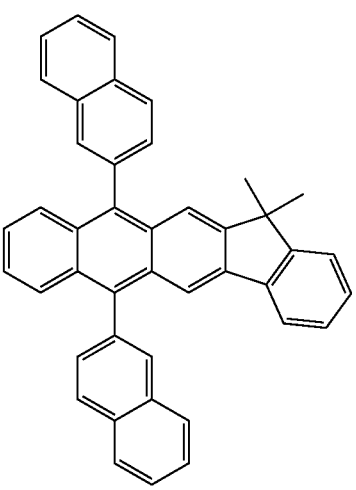
H38
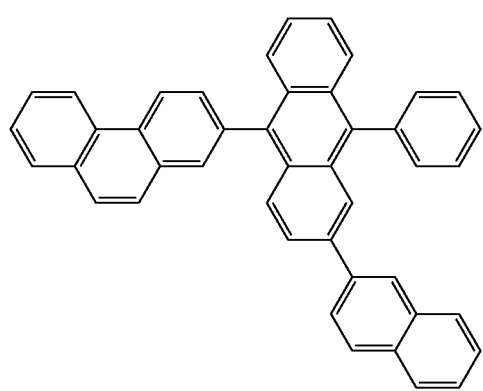
H41
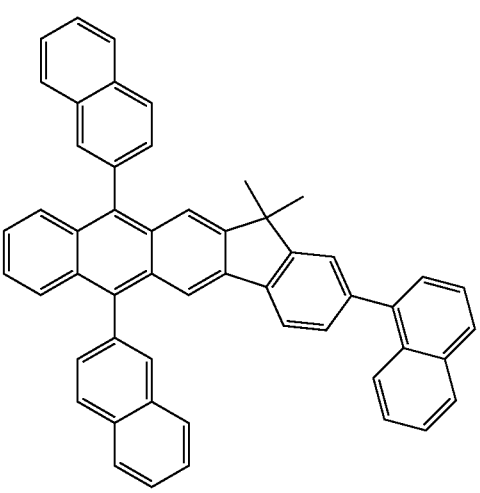

H42
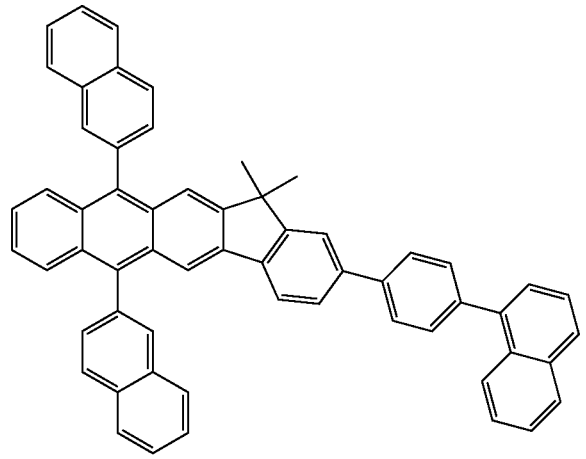
Also, the host may include at least one of Compounds H43 to H49, but is not limited thereto:
H43
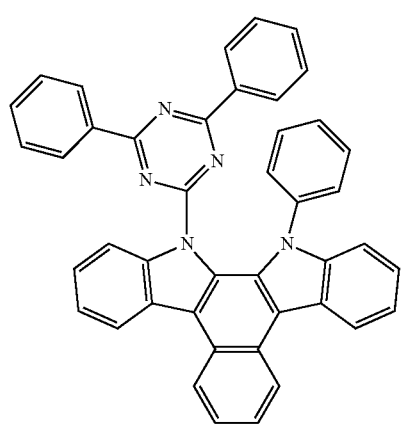
H44
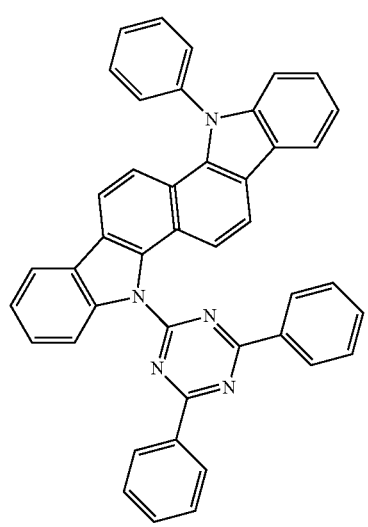
H45
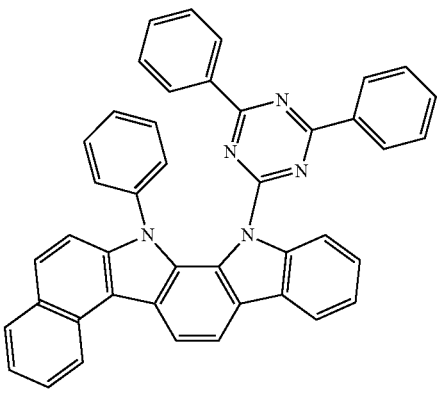
H46
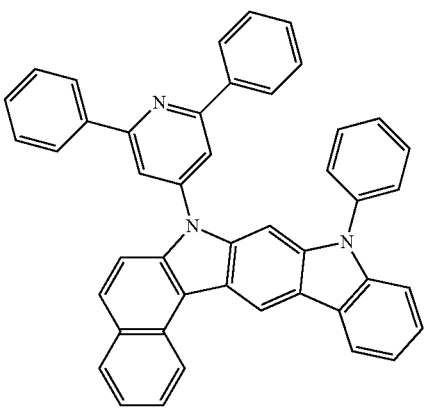
H47
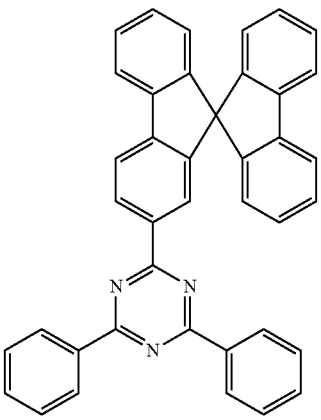
H48
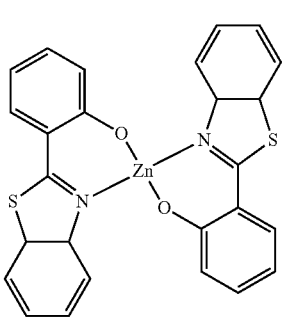

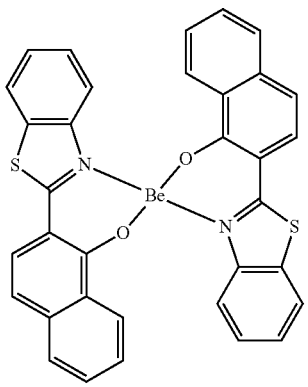

H49

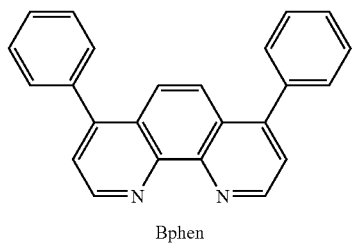

Bphen

The dopant may include the condensed cyclic compound represented by Formula 1.

In one embodiment, an amount of the dopant in the EML may be from a range of about 0.01 part to about 15 parts by weight based on about 100 parts by weight of the host, but is not limited thereto.

A thickness of the EML may be in a range of about 100 Å to about 1,000 Å, for example, about 200 Å to about 600 Å. In one embodiment, when a thickness of the EML is within this range, the OLED 10 has excellent light-emitting properties without a substantial increase in driving voltage.

Next, an electron transport region may be disposed on the EML.

The electron transport region may include at least one of an HBL, an ETL, and an EIL, but is not limited thereto.

For example, the electron transport region may have a structure including ETL, ELT/EIL, or HBL/ETL/EIL sequentially stacked on the EML, but the structure is not limited thereto.

According to one embodiment, the organic layer 15 of the OLED 10 may include an electron transport region disposed between the EML and the second electrode 17.

The electron transport region may include an HBL. When the EML includes a phosphorescent dopant, the HBL may be formed to prevent diffusion of triplet excitons or holes into the electron transport layer.

When the electron transport region includes an HBL, the HBL may be formed on the EML by using (utilizing) various suitable methods, such as a vacuum deposition method, a spin-coating method, a cast method, an LB method, an inkjet printing method, a laser printing method, or an LITI method. When the HBL is formed by using (utilizing) a vacuum deposition method or a spin-coating method, the deposition conditions and the coating conditions of the HBL may be referenced or referred to the deposition conditions and the coating conditions of the HIL.

The HBL may include, for example, at least one of BCP and Bphen, but is not limited thereto:

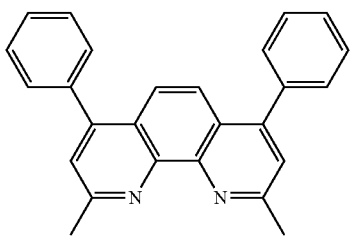

BCP

A thickness of the HBL may be in a range of about 20 Å to about 1,000 Å, for example, about 30 Å to about 300 Å. In one embodiment, when a thickness of the HBL is within this range, excellent hole blocking properties are obtained without a substantial increase in driving voltage.

The electron transport region may include an ETL. The ETL may be formed on the EML or the HBL by using (utilizing) various suitable methods, such as a vacuum deposition method, a spin-coating method, a cast method, an LB method, an inkjet printing method, a laser printing method, or an LITI method. When the ETL is formed by using (utilizing) a vacuum deposition method or a spin-coating method, the deposition conditions and the coating conditions of the HBL may be referenced or referred to the deposition conditions and the coating conditions of the HIL.

The ETL may include, for example, at least one of BCP, Bphen, $Alq_3$, Balq, TAZ, and NTAZ, but is not limited thereto:

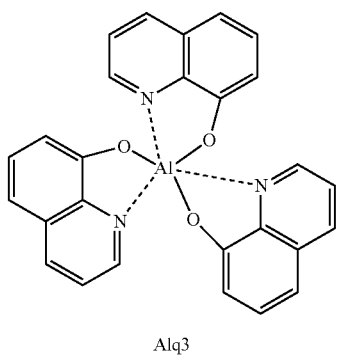

Alq3

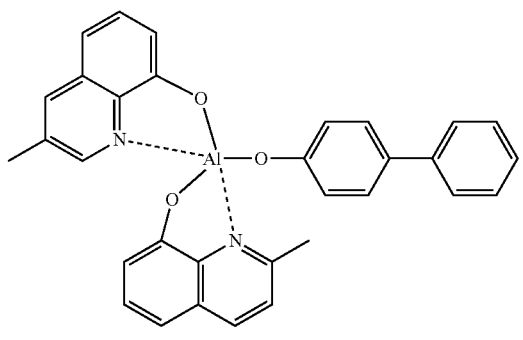

BAlq

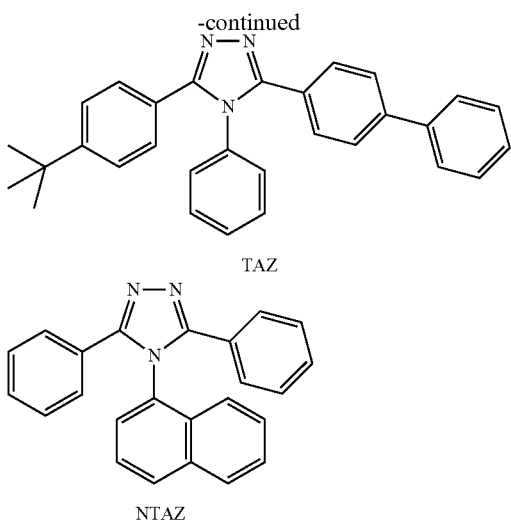

TAZ

NTAZ

Also, the ETL may include at least one of compounds represented by Formula 601:

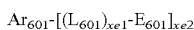

Ar$_{601}$-[(L$_{601}$)$_{xe1}$-E$_{601}$]$_{xe2}$    Formula 601

In Formula 601, the description of Ar$_{601}$ may be referenced or referred to the description of Ar$_{301}$ in the present specification;

the description of L$_{601}$ may be referenced or referred to the description of L$_{201}$ in the present specification;

E$_{601}$ may be selected from:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;

xe1 is selected from 0, 1, 2, and 3; and xe2 is selected from 1, 2, 3, and 4.

Also, the ETL may include at least one of compounds represented by Formula 602:

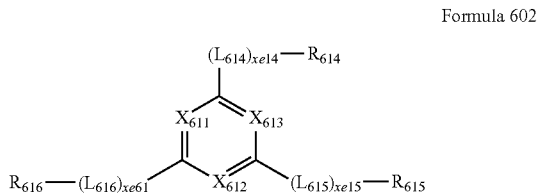

Formula 602

In Formula 602, $X_{611}$ is N or C-(L$_{611}$)$_{xe611}$-R$_{611}$, $X_{612}$ is N or C-(L$_{612}$)$_{xe612}$-R$_{612}$, $X_{613}$ is N or C-(L$_{613}$)$_{xe613}$-R$_{613}$, at least one of $X_{611}$ to $X_{613}$ is N;

the description of each of L$_{611}$ to L$_{616}$ is referred to the description of L$_{201}$ in the present specification;

R$_{611}$ to R$_{616}$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 are each independently selected from 0, 1, 2, and 3.

The compound represented by Formula 601 and the compound represented by Formula 602 may include at least one of Compounds ET1 to ET15:

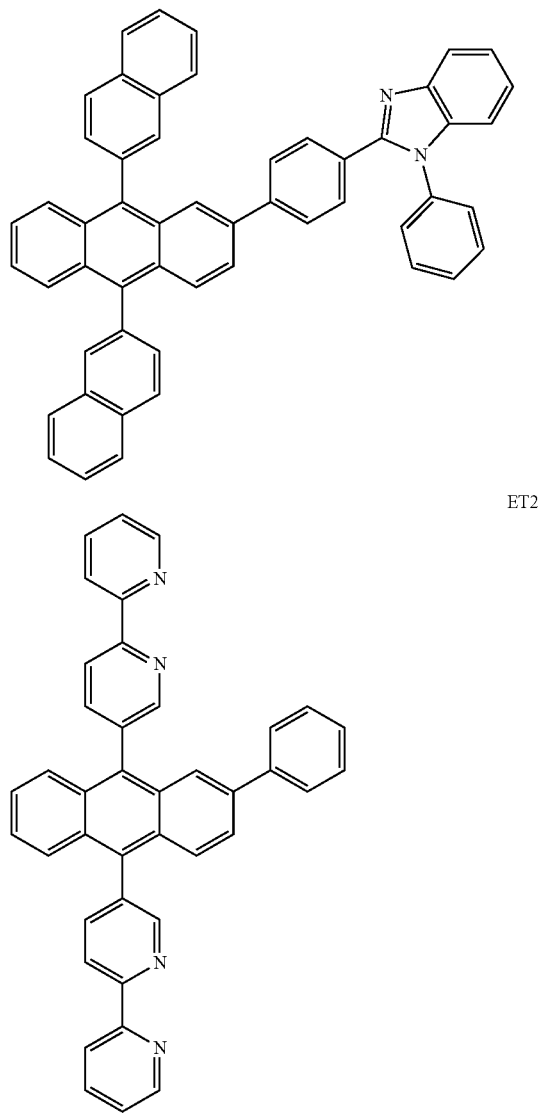

ET1

ET2

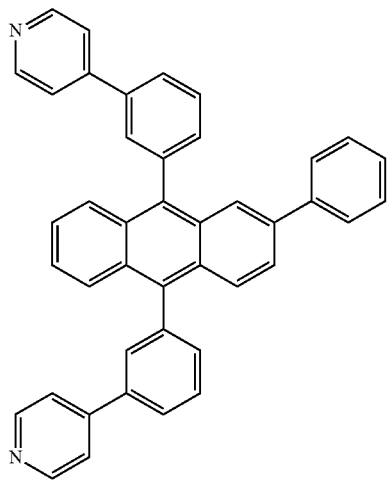

ET3

ET4

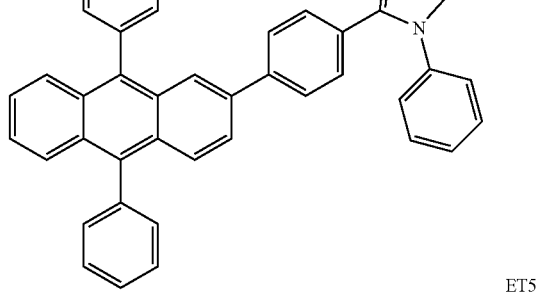

ET5

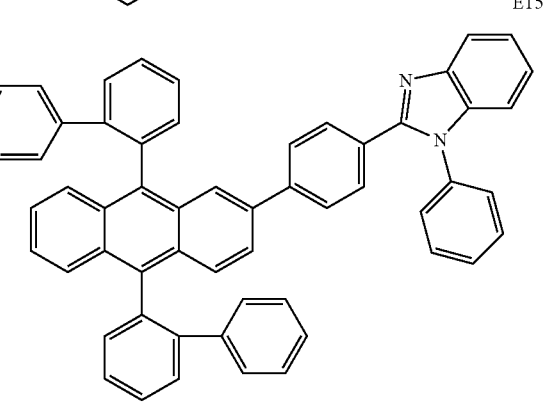

ET6

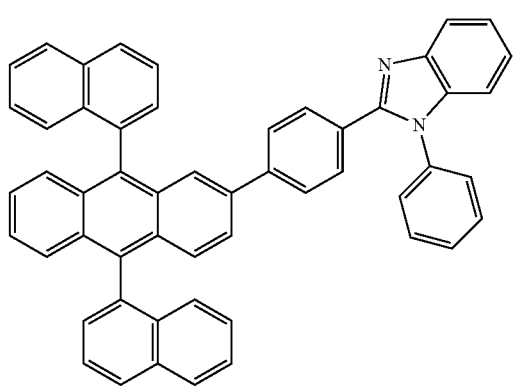

-continued
ET7
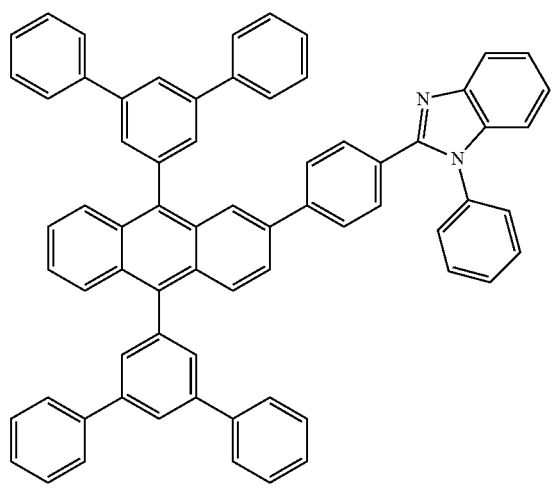
ET8
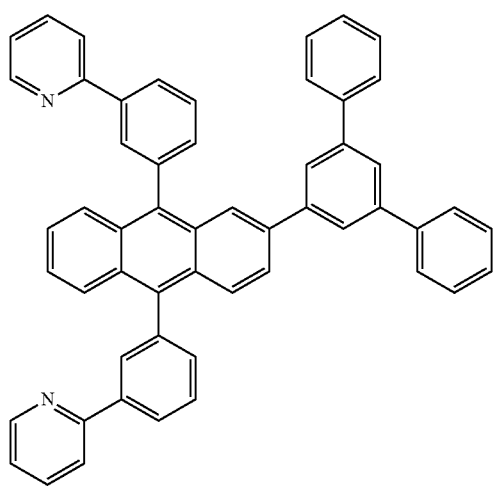
ET9
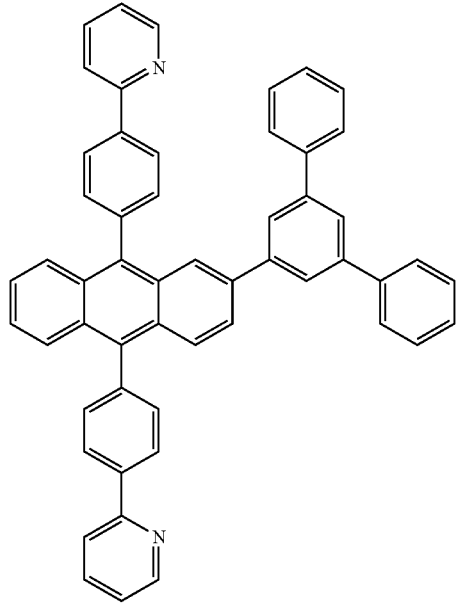
-continued
ET10
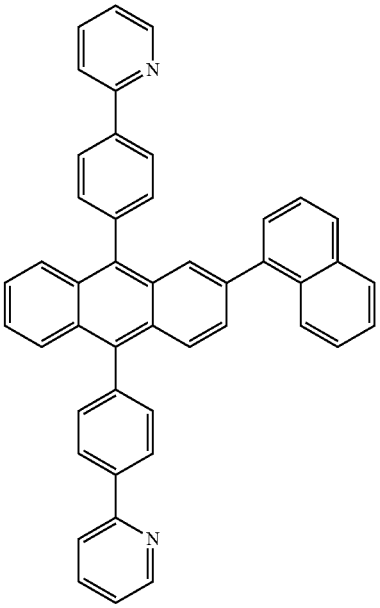
ET11
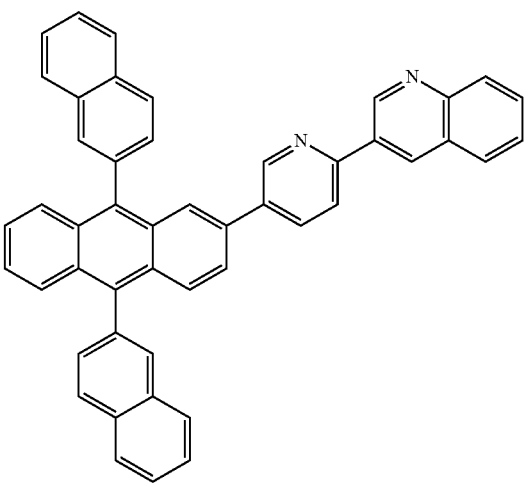
ET12
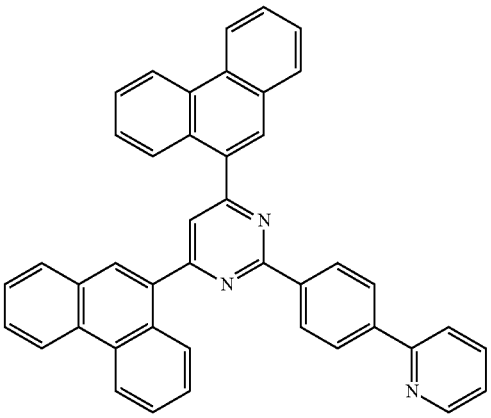

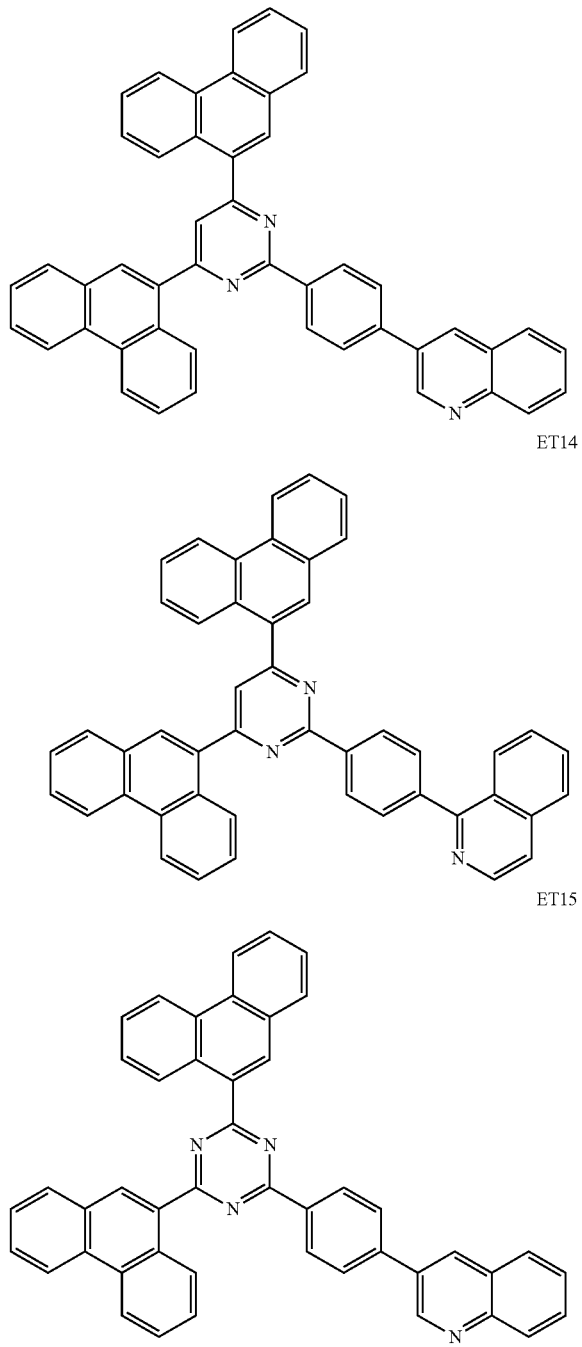

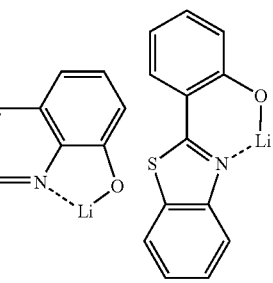

ET-D1        ET-D2

The electron transport region may include an EIL that facilitates injection of electrons from the second electrode 17.

The EIL may be formed on the ETL by using (utilizing) various suitable methods, such as a vacuum deposition method, a spin-coating method, a cast method, an LB method, an inkjet printing method, a laser printing method, or an LITI method. When the EIL is formed by using (utilizing) a vacuum deposition method or a spin-coating method, the deposition conditions and the coating conditions of the EML may be referenced or referred to the deposition conditions and the coating conditions of the HIL.

The EIL may include at least one selected from LiF, NaCl, CsF, $Li_2O$, BaO, and LiQ.

A thickness of the EIL may be in a range of about 1 Å to about 100 Å, for example, about 3 Å to about 90 Å. In one embodiment, when a thickness of the EIL is within this range, excellent electron injecting properties are obtained without a substantial increase in driving voltage.

The second electrode 17 is disposed on the organic layer 15 described above. The second electrode 17 may be an electron injection electrode, that is, a cathode. A material for forming the second electrode 17 may include a metal having a low work function, an alloy, an electrically conductive compound, or a mixture thereof. Examples of the material for forming the second electrode 17 may include lithium (Li), magnesium (Mg), aluminum (Al), aluminum-lithium (Al—Li), calcium (Ca), magnesium-indium (Mg—In), and magnesium-silver (Mg—Ag). In addition, examples of the material for forming the second electrode 17 may include ITO and IZO. The second electrode 17 may be a reflective electrode, a semi-transparent electrode, or a transparent electrode.

Thus far, an OLED has been described by referring to the drawing, but an OLED is not limited thereto. For example, the OLED 10 of the drawing has the substrate 11 located under the first electrode 13, but, optionally, the substrate 11 may be located on the second electrode 17.

As used herein, the term "alkyl group" refers to a linear or branched aliphatic monovalent hydrocarbon group. Examples of the alkyl group include a methyl group, an ethyl group, a propyl group, an isobutyl group, a sec-butyl group, a tert-butyl group, a pentyl group, an iso-amyl group, and a hexyl group. As used herein, the term "alkylene group" refers to a divalent group having the same structure as the alkyl group.

A thickness of the ETL may be in a range of about 100 Å to about 1,000 Å, for example, about 150 Å to about 500 Å. In one embodiment, when a thickness of the ETL is within this range, excellent electron transporting properties are obtained without a substantial increase in driving voltage.

The electron transport layer may include a metal-containing material in addition to the materials stated above.

The metal-containing material may include a Li-complex. The Li-complex may include, for example, Compound ET-D1, which is a lithium quinolate (LiQ), or Compound ET-D2:

As used herein, the term "alkoxy group" refers to a monovalent group having a formula of $-OA_{101}$ (where, $A_{101}$ is the $C_1$-$C_{60}$ alkyl group). Examples of the alkoxy group include a methoxy group, an ethoxy group, and an isopropoxy group.

As used herein, the term "alkenyl group" refers to the alkyl group having at least one carbon double bond in the middle or at an end thereof. Examples of the alkenyl group include an ethenyl group, a prophenyl group, and a butenyl group. As used herein, the term "alkenylene group" refers to a divalent group having the same structure as the alkenyl group.

As used herein, the term "alkynyl group" refers to the alkyl group having at least one carbon triple bond in the middle or at the end thereof. Examples of the alkynyl group include an ethynyl group and a propynyl group. As used herein, the term "alkynylene group" refers to a divalent group having the same structure as the alkynyl group.

As used herein, the term "cycloalkyl group" refers to a monovalent saturated hydrocarbon monocyclic group. Examples of the cycloalkyl group include a cyclopropyl group, a cyclobutyl group, a cyclopentyl group, a cyclohexyl group, and a cycloheptyl group. As used herein, the term "cycloalkylene group" refers to a divalent group having the same structure as cycloalkyl group".

As used herein, the term "heterocycloalkyl group" refers to a monovalent monocyclic group including at least one heteroatom selected from N, O, P, and S as a ring-forming atom. Examples of the heterocycloalkyl group include a tetrahydrofuranyl group and a tetrahydrothiophenyl group. As used herein, the term "heterocycloalkylene group" refers to a divalent group having the same structure as the heterocycloalkyl group.

As used herein, the term "cycloalkenyl group" refers to a monovalent monocyclic group having at least one double bond that does not have aromaticity. Examples of the heterocycloalkyl group include a cyclopentenyl group, a cyclohexenyl group, and a cycloheptenyl group. As used herein, the term "cycloalkenylene group" refers to a divalent group having the same structure as the cycloalkenyl group.

As used herein, the term "heterocycloalkenyl group" refers to a monovalent monocyclic group including at least one heteroatom selected from N, O, P, and S as a ring-forming atom and having at least one double bond in the ring. Examples of the heterocycloalkenyl group include a 2,3-hydrofuranyl group and a 2,3-hydrothiophenyl group. As used herein, the term "heterocycloalkenylene group" refers to a divalent group having the same structure as the heterocycloalkenyl group.

As used herein, the term "aryl group" refers to a monovalent group having a carbocyclic aromatic system, and the term "arylene group" refers to a divalent group having a carbocyclic aromatic system. Examples of the aryl group include a phenyl group, a naphthyl group, an anthracenyl group, a phenanthrenyl group, a pyrenyl group, and a chrysenyl group. When the aryl group and the arylene group include two or more rings, the rings may be fused to each other.

As used herein, the term "heteroaryl group" refers to a monovalent group having a carbocyclic aromatic system including at least one heteroatom selected from N, O, P, and S as a ring-forming atom, and the term "heteroarylene group" refers to a divalent group having a carbocyclic aromatic system including at least one heteroatom selected from N, O, P, and S as a ring-forming atom. Examples of the heteroaryl group include a pyridinyl group, a pyrimidinyl group, a pyrazinyl group, a pyridazinyl group, a triazinyl group, a quinolinyl group, and an isoquinolinyl group. When the heteroaryl group and the heteroarylene group include two or more rings, the rings may be fused to each other.

As used herein, the term "aryloxy group" refers to $-OA_{102}$ (where, $A_{102}$ is the aryl group), and the term "arylthio group" refers to $-SA_{103}$ (where, $A_{103}$ is the aryl group).

As used herein, the term "monovalent non-aromatic condensed polycyclic group" refers to a monovalent group having two or more rings that are fused to each other, wherein the whole molecule has non-aromacity. The monovalent non-aromatic condensed polycyclic group includes i) only carbon (C), or ii) a heteroatom selected from N, O, P, and S, other than C, as a ring-forming atom. Examples of the non-aromatic condensed polycyclic group include a heptalenyl group and a triquinacenyl group. As used herein, the term "divalent non-aromatic condensed polycyclic group" refers to a divalent group having the same structure as the monovalent non-aromatic condensed polycyclic group.

As used herein, the term "$C_m$-$C_n$ (m<n)" refers to the number of carbon atoms being m to n. For example, a $C_1$-$C_{10}$ alkyl group refers to an alkyl group having one to ten carbon atoms, and a $C_6$-$C_{30}$ aryl group refers to an aryl group having six to thirty carbon atoms.

As used herein, the term "Ph" refers to phenyl, "Me" to methyl, "Et" to ethyl, and "ter-Bu" or "Bu$^t$" to tert-butyl.

Hereinafter, an OLED according to an embodiment of the present invention will be described in more detail with reference to the following synthesis examples and other examples. The expression "A is used (utilized) instead of B" in the synthesis examples denotes that a molar amount of A and a molar amount of B are the same.

Synthesis Example 1

Synthesis of Compound 5

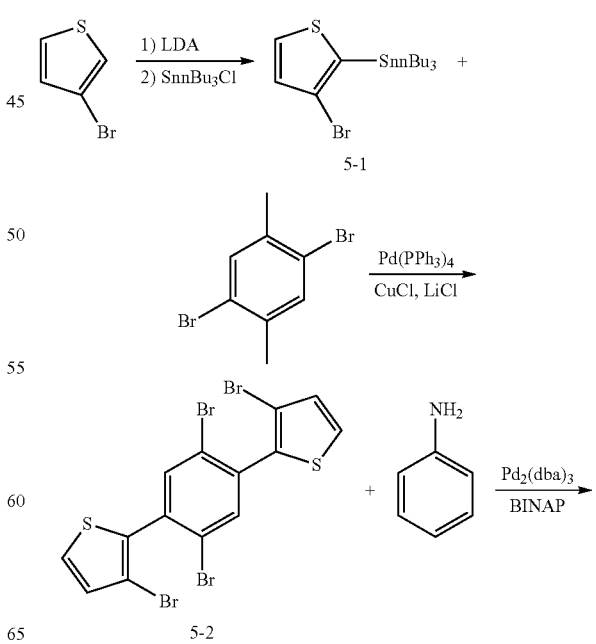

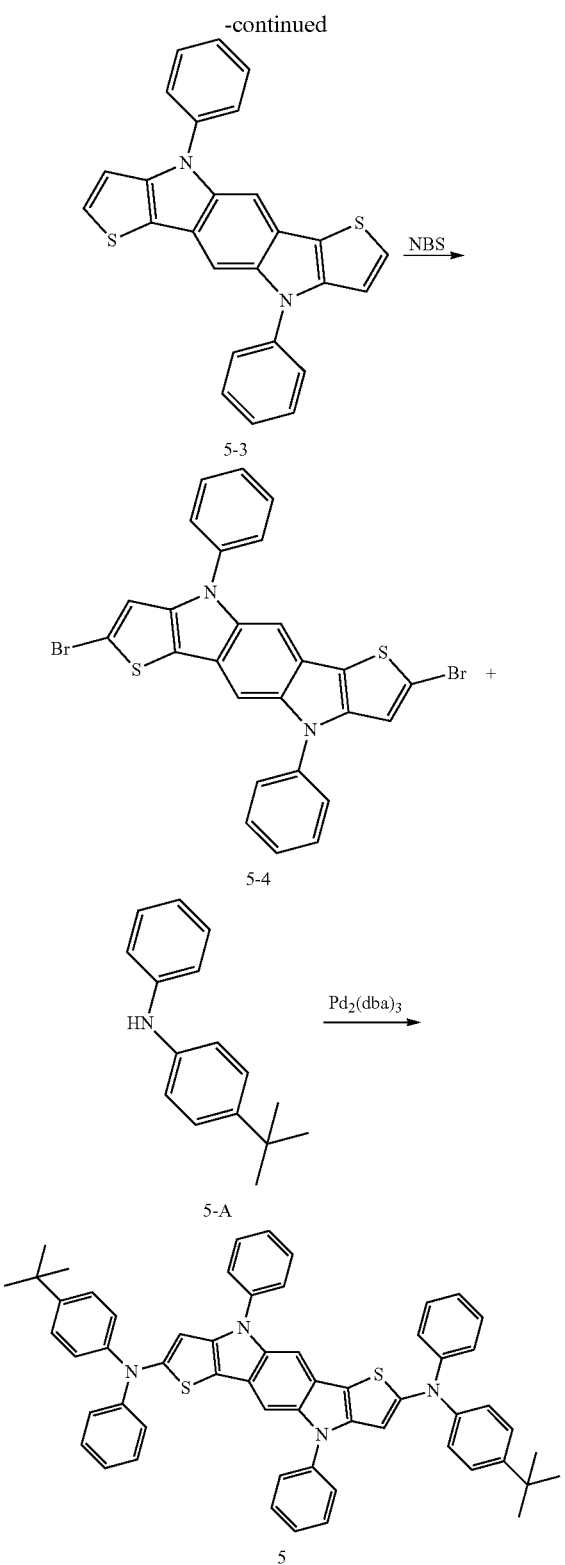

Synthesis of Intermediate 5-1

11.1 g (110.0 mmol) of a diisopropylamine was dissolved in 100 mL of anhydrous tetrahydrofuran (THF), and 44.4 mL (110.0 mmol, 2.5 M in Hexane) of n-BuLi was slowly and dropwisely added to the solution at a temperature of −20° C. to synthesize a lithium diisopropylamide (LDA) solution. The solution was stirred at the same temperature for 5 minutes, and then the solution was stirred for 20 minutes after increasing the temperature to room temperature. The solution was slowly and dropwisely added to a solution prepared by dissolving 18.1 g (110.0 mmol) of 3-bromothiophen in 50 mL of THF at a temperature of −20° C. After stirring for 2 hours at the same temperature, 35.8 g (110 mmol) of tributyltin chloride was added at once, and the mixture was stirred for 12 hours after increasing the temperature to room temperature. When the reaction was completed, 50 mL of $H_2O$ was added, and then the mixture was extracted 3 times using (utilizing) 80 mL of hexane. The organic layer collected therefrom was dried using (utilizing) magnesium sulfate, and then the solvent was evaporated to collect 35.7 g of Intermediate 5-1 (yield: 72%). The compound was confirmed by LC-MS. $C_{16}H_{29}BrSSn$: $M^+$ 452.1.

Synthesis of Intermediate 5-2

4.8 g (10.0 mmol) of 2,5-dibromo-1,4-diiodobenzene, 2.7 g (60.0 mmol) of LiCl, 5.0 g (50 mmol) of CuCl, and 0.29 g (0.25 mmol) of tetrakis(triphenylphosphine)palladium (Pd$(PPh_3)_4$) were added to a Schlenk tube, and after removing a gas therefrom, a nitrogen atmosphere was formed in the tube. 60 mL of DMSO was added to the tube, 4.97 g (11 mmol) of Intermediate 5-1 was added thereto, the mixture in the tube was stirred for 1 hour at room temperature, and then the mixture was stirred for another 3 hours at a temperature of 50° C. The reaction solution was cooled to room temperature, and the precipitate obtained therefrom was filtered to obtain 2.2 g (yield: 40%) of Intermediate 5-2. The compound was confirmed by LC-MS. $C_{14}H_6Br_4S_2$: $M^+$ 553.6.

Synthesis of Intermediate 5-3

5.58 g (10.0 mmol) of Intermediate 5-2, 0.92 g (1.0 mmol) of $Pd_2(dba)_3$, 1.24 g (2.0 mmol) of 2,2'-bis(diphenylphosphino)-1,1'-binaphthyl (BINAP), and 7.68 g (80.0 mmol) of NaOtBu were added, and after removing a gas therefrom, the mixture was dissolved in 5.16 g (40 mmol) of aniline and 100 ml of p-xylene. The solution was stirred at a temperature of 100° C. for 2 hours. The reaction solution was cooled to room temperature and extracted 3 times using (utilizing) 50 mL of water and 50 mL of methylene chloride. The organic layer collected therefrom was dried using (utilizing) magnesium sulfate, the solvent was evaporated, and then resulting residues were separated and purified using (utilizing) silicagel tube column chromatography to obtain 2.73 g of Intermediate 5-3 (yield: 65%). The compound was confirmed by LC-MS. $C_{26}H_{16}N_2S_2$ $M^+$ 420.1.

Synthesis of Intermediate 5-4

0.84 g (2.00 mmol) of Intermediate 5-3 was dissolved in 50 mL of methylene chloride (MC) to prepare a mixture, and 0.72 g (4.0 mmol) of N-bromosuccinimide (NBS) was slowly and dropwisely added to the mixture at room temperature and stirred for 24 hour. When the reaction was completed, 50 mL of $H_2O$ was added, and then the mixture was extracted 3 times using (utilizing) 50 mL of MC. The organic layer collected therefrom was dried using (utilizing) magnesium sulfate, the solvent was evaporated, and then resulting residues were separated and purified using (utilizing) silicagel tube column chromatography to obtain 0.91 g of Intermediate 5-4 (yield: 79%). The compound was confirmed by LC-MS. $C_{26}H_{14}Br_2N_2S_2$: M+ 575.9.

Synthesis Compound 5

1.15 g (2.0 mmol) of Intermediate 5-4, 0.90 g (4.0 mmol) of Compound 5-A, 37 mg (0.04 mmol) of $Pd_2(dba)_3$, 8 mg (0.04 mmol) of $PtBu_3$, and 0.58 g (6.0 mmol) of KOtBu were dissolved in 30 ml of toluene, and the mixture was stirred at a temperature of 85° C. for 12 hours. The reaction solution was cooled to room temperature and extracted 3 times using (utilizing) 30 mL of water and 30 mL of diethylether. The organic layer collected therefrom was dried using (utilizing) magnesium sulfate, the solvent was evaporated, and then resulting residues were separated and purified using (utilizing) silicagel tube column chromatography to obtain 1.44 g of Compound 5 (yield: 83%). The compound was confirmed by LC-MS. $C_{58}H_{50}N_4S_2$: M+ 866.36.

Synthesis Example 2

Synthesis of Compound 13

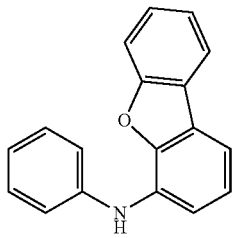

13-A

Compound 13 was synthesized by using (utilizing) the same manner used (utilized) to synthesize Compound 5, except that Compound 13-A was used (utilized) instead of Intermediate 5-A in the method used (utilized) to synthesize Compound 5 in Synthesis Example 1. The obtained compound was confirmed by LC-MS. $C_{62}H_{38}N_4O_2S_2$: M+ 934.25.

Synthesis Example 3

Synthesis of Compound 22

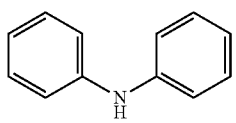

22-A

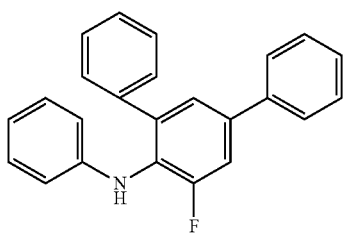

22-B

Compound 22 was synthesized by using (utilizing) the same manner used (utilized) to synthesize Compound 5, except that Compound 22-A and Compound 22-B were sequentially used (utilized) instead of Intermediate 5-A in the method used (utilized) to synthesize Compound 5 in Synthesis Example 1. The obtained compound was confirmed by LC-MS. $C_{62}H_{41}FN_4S_2$: M+ 924.29.

Synthesis Example 4

Synthesis of Compound 37

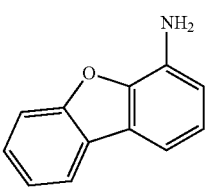

37-A

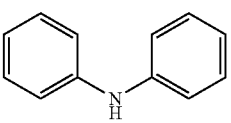

37-B

Compound 37 was synthesized by using (utilizing) the same manner used (utilized) in Synthesis Example 1, except that Intermediate 37-A was used (utilized) instead of aniline in the method used (utilized) to synthesize Intermediate 5-3, and Intermediate 37-B was used (utilized) instead of Compound 5-A in the method used (utilized) to synthesize Compound 5. The obtained compound was confirmed by LC-MS. $C_{62}H_{38}N_4O_2S_2$: M+ 934.25.

Synthesis Example 5

Synthesis of Compound 52

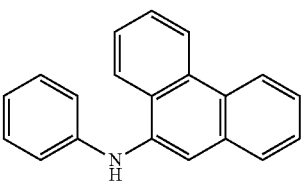

52-A

Compound 52 was synthesized by using (utilizing) the same manner used (utilized) in Synthesis Example 1, except that ethylamine was used (utilized) instead of aniline in the method used (utilized) to synthesize Intermediate 5-3, and Compound 52-A was used (utilized) instead of Compound 5-A in the method used (utilized) to synthesize Compound 5. The obtained compound was confirmed by LC-MS. $C_{58}H_{42}N_4S_2$: M+ 858.30.

A synthesis method including the same synthesis pathways and appropriate intermediate materials were used (utilized) to synthesize additional compounds, and the $^1H$ NMR and MS/FAB results of the synthesized compounds are shown in Table 1.

It may be obvious to one of ordinary skill in the art to recognize compounds other than the compounds shown in Table 1 by using (utilizing) the synthesis method with reference to the synthesis pathways and the raw materials.

TABLE 1

| Compound | ¹H NMR (CDCl₃, 400 MHz) δ | MS/FAB found | calc. |
|---|---|---|---|
| 1 | δ = 8.20 (s, 2H), 7.59-7.51 (m, 8H), 7.40-7.35 (m, 2H), 7.31-7.24 (m, 8H), 7.20-7.14 (m, 8H), 7.06-7.02 (m, 4H), 6.61 (s, 2H) | 754.23 | 754.22 |
| 5 | δ = 8.20 (S, 2H), 7.56-7.51 (m, 8H), 7.42-7.38 (m, 2H), 7.32-7.27 (m, 8H), 7.19-7.16 (m, 4H), 7.06-7.04 (m, 2H), 6.61-6.57 (m, 4H), 6.42 (s, 2H), 1.41 (s, 18H) | 866.36 | 866.35 |
| 6 | δ = 8.20 (s, 2H), 7.58-7.52 (m, 8H), 7.48-7.44 (m, 4H), 7.40-7.36 (m, 2H), 7.32-7.27 (m, 4H), 7.18-7.15 (m, 4H), 7.08-7.05 (m, 4H), 7.07-7.02 (m, 2H), 6.85-6.82 (m, 4H), 6.42 (s, 2H), 0.24 (s, 18H) | 898.30 | 898.30 |
| 8 | δ = 8.20 (s, 2H), 7.58-7.51 (m, 8H), 7.40-7.36 (m, 2H), 7.31-7.25 (m, 4H), 7.20-7.17 (m, 4H), 7.05-7.02 (m, 2H), 6.97-6.89 (m, 4H), 6.76-6.72 (m, 2H), 6.37 (s, 2H) | 826.19 | 826.18 |
| 13 | δ = 8.20 (s, 2H), 7.84-7.82 (m, 2H), 7.72-7.68 (m, 2H), 7.62-7.52 (m, 10H), 7.46-7.29 (m, 10H), 7.13-7.01 (m, 10H), 6.36 (s, 2H) | 934.25 | 934.24 |
| 15 | δ = 8.20 (s, 2H), 8.06-8.04 (m, 2H), 7.83-7.76 (m, 4H), 7.76-7.74 (m, 2H), 7.62-7.51 (m, 10H), 7.48-7.26 (m, 8H), 7.17-7.14 (m, 4H), 7.08-7.01 (m, 4H), 6.46 (s, 2H) | 966.21 | 966.20 |
| 18 | δ = 8.59-8.57 (m, 1H), 8.20 (s, 2H), 8.16-8.14 (m, 1H), 7.74-7.51 (m, 12H), 7.43-7.36 (m, 4H), 7.32-7.24 (m, 6H), 7.17-7.13 (m, 5H), 7.09-7.02 (m, 5H), 6.41 (s, 1H), 6.27 (s, 1H) | 854.26 | 854.25 |
| 22 | δ = 8.20 (s, 2H), 7.86-7.84 (m, 2H), 7.72-7.68 (m, 3H), 7.65-7.51 (m, 13H), 7.44-7.38 (m, 3H), 7.32-7.25 (m, 4H), 7.24-7.00 (m, 12H), 6.41 (s, 1H), 6.32 (s, 1H) | 924.29 | 924.28 |
| 23 | δ = 8.20 (s, 2H), 8.01-7.99 (m, 1H), 7.82-7.72 (m, 5H), 7.59-7.51 (m, 12H), 7.44-7.36 (m, 5H), 7.32-7.27 (m, 4H), 7.17-7.14 (m, 4H), 7.08-7.02 (m, 3H), 6.49 (s, 1H), 6.31 (s, 1H) | 894.26 | 894.25 |
| 25 | δ = 8.20 (s, 2H), 7.59-7.51 (m, 8H), 7.40-7.31 (m, 4H), 7.15-7.12 (m, 2H), 7.09-7.06 (m, 1H), 6.93-6.90 (m, 3H), 6.60-6.55 (m, 5H), 6.45-6.42 (m, 3H), 2.37-2.34 (m, 18H) | 838.33 | 838.32 |
| 27 | δ = 8.59-7.55 (m, 3H), 8.20 (s, 2H), 8.16-8.14 (m, 1H), 7.90-7.88 (m, 1H), 7.74-7.63 (m, 3H), 7.58-7.51 (m, 9H), 7.43-7.36 (m, 4H), 7.35-7.27 (m, 4H), 7.17-7.14 (m, 4H), 7.08-7.05 (m, 2H), 6.61-6.59 (m, 2H), 6.50 (s, 1H), 6.41 (s, 1H) | 855.26 | 855.25 |
| 29 | δ = 8.24 (s, 2H), 7.93-7.90 (m, 2H), 7.85-7.83 (m, 2H), 7.73-7.70 (m, 4H), 7.65-7.61 (m, 2H), 7.53-7.51 (m, 2H), 7.44-7.40 (m, 2H), 7.32-7.27 (m, 8H), 7.19-7.14 (m, 8H), 7.08-7.04 (m, 4H), 6.45 (s, 2H) | 854.26 | 854.25 |
| 31 | δ = 8.22 (s, 2H), 7.63-7.60 (m, 4H), 7.52-7.38 (m, 14H), 7.32-7.27 (m, 8H), 7.18-7.14 (m, 8H), 7.08-7.04 (m, 4H), 6.42 (s, 2H) | 906.30 | 906.29 |
| 33 | δ = 8.67-8.64 (m, 4H), 7.98-7.96 (m, 2H), 7.69-7.65 (m, 2H), 7.32-7.26 (m, 10H), 7.20-7.15 (m, 8H), 7.08-7.04 (m, 4H), 6.64 (s, 2H) | 756.22 | 756.21 |
| 35 | δ = 8.22 (s, 2H), 7.39-7.27 (m, 12H), 7.18-7.04 (m, 16H), 6.42 (s, 2H) | 790.21 | 790.20 |
| 37 | δ = 8.12 (s, 2H), 7.91-7.88 (m, 2H), 7.81-7.79 (m, 2H), 7.75-7.73 (m, 2H), 7.60-7.54 (m, 4H), 7.40-7.36 (m, 2H), 7.32-7.27 (m, 10H), 7.18-7.14 (m, 8H), 7.08-7.04 (m, 4H), 6.38 (s, 2H) | 934.25 | 934.24 |
| 38 | δ = 8.29-8.27 (m, 2H), 8.23 (s, 2H), 8.06-8.04 (m, 2H), 7.88-7.86 (m, 2H), 7.70-7.66 (m, 2H), 7.58-7.54 (m, 2H), 7.46-7.42 (m, 2H), 7.33-7.27 (m, 10H), 7.17-7.14 (m, 8H), 7.05-7.02 (m, 4H), 6.46 (s, 2H) | 966.21 | 966.20 |
| 39 | δ = 8.22 (s, 2H), 7.61-7.57 (m, 4H), 7.47-7.44 (m, 4H), 7.32-7.27 (m, 8H), 7.18-7.10 (m, 8H), 7.08-7.04 (m, 4H), 6.42 (s, 2H), 0.26 (s, 18H) | 898.31 | 898.30 |
| 43 | δ = 8.58-8.55 (m, 4H), 8.25 (s, 2H), 7.78-7.71 (m, 6H), 7.59-7.53 (m, 4H), 7.41-7.36 (m, 6H), 7.32-7.28 (m, 6H), 7.18-7.13 (m, 4H), 7.08-7.04 (m, 2H), 6.57 (s, 2H) | 856.25 | 856.24 |
| 45 | δ = 8.67-8.64 (m, 4H), 7.98-7.95 (m, 2H), 7.78-7.47 (m, 12H), 7.42-7.37 (m, 4H), 7.35-7.26 (m, 6H), 7.17-7.14 (m, 4H), 7.08-7.04 (m, 2H), 6.94-6.90 (m, 2H), 6.70 (s, 1H), 6.64 (s, 1H) | 882.27 | 882.26 |
| 47 | δ = 7.73 (s, 2H), 7.32-7.27 (m, 8H), 7.18-7.10 (m, 8H), 7.08-7.04 (m, 4H), 6.51 (s, 2H), 1.87 (s, 18H) | 714.30 | 714.29 |
| 48 | δ = 7.78-7.76 (m, 2H), 7.73-7.68 (m, 6H), 7.59-7.53 (m, 4H), 7.41-7.39 (m, 2H), 7.33-7.28 (m, 6H), 7.17-7.14 (m, 4H), 7.08-7.04 (m, 2H), 6.56 (s, 2H), 1.87 (s, 18H) | 814.33 | 814.32 |
| 51 | δ = 8.25 (s, 2H), 7.78-7.76 (m, 2H), 7.54-7.52 (m, 2H), 7.36-7.28 (m, 6H), 7.18-7.15 (m, 4H), 7.11-7.04 (m, | 890.36 | 890.35 |

TABLE 1-continued

| Compound | $^1$H NMR (CDCl$_3$, 400 MHz) δ | MS/FAB found | calc. |
|---|---|---|---|
| | 6H), 6.95-6.93 (m, 2H), 6.66-6.63 (m, 2H), 6.36 (s, 2H), 4.27-4.21 (m, 4H), 1.61 (s, 12H), 1.41-1.37 (m, 6H) | | |
| 52 | δ = 8.59-8.57 (m, 2H), 8.25 (s, 2H), 8.16-8.14 (m, 2H), 7.90-7.88 (m, 2H), 7.74-7.55 (m, 8H), 7.43-7.39 (m, 2H), 7.29-7.24 (m, 4H), 7.13-7.02 (m, 8H), 6.37 (s, 2H), 4.27-4.23 (m, 4H), 1.41-1.37 (m, 6H) | 858.30 | 858.29 |

Example 1

An ITO glass substrate (Corning) having a thickness of 15 Ω/cm$^2$ (1,200 Å) was cut into a size of 50 mm×50 mm×0.7 mm, sonicated in isopropyl alcohol for 5 minutes and pure water for 5 minutes, and cleaned by irradiating ultraviolet rays for 30 minutes and exposing to ozone. Then, the ITO glass substrate was placed into a vacuum deposition chamber.

2-TNATA was deposited on the ITO glass substrate (an anode) to form an HIL having a thickness of 600 Å. Then, NPB was deposited on the HIL to form an HTL having a thickness of 300 Å, and ADN (a host) and Compound 5 (a dopant) were co-deposited at a weight ratio of 98:2 on the HTL to form an EML having a thickness of 300 Å.

The Alq$_3$ was deposited on the EML to form an ETL having a thickness of 300 Å, and LiF was deposited on the ETL to form an EIL having a thickness of 10 Å. Then, Al was deposited on the EIL to form a cathode having a thickness of 3000 Å, thereby completing an OLED.

Example 2

An OLED was manufactured in the same manner as in Example 1, except that Compound 13 was used (utilized) instead of Compound 5 when forming the EML.

Example 3

An OLED was manufactured in the same manner as in Example 1, except that Compound 22 was used (utilized) instead of Compound 5 when forming the EML.

Example 4

An OLED was manufactured in the same manner as in Example 1, except that Compound 37 was used (utilized) instead of Compound 5 when forming the EML.

Example 5

An OLED was manufactured in the same manner as in Example 1, except that Compound 52 was used (utilized) instead of Compound 5 when forming the EML.

Comparative Example 1

An OLED was manufactured in the same manner as in Example 1, except that Compound A was used (utilized) instead of Compound 3 when forming the EML.

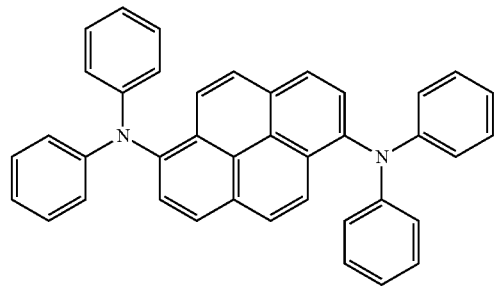

Compound A

Evaluation Example 1

In regard of the OLEDs prepared in Examples 1 to 5 and Comparative Example 1, driving voltages, current densities, brightness, efficiencies, colors of emitted light, and half-life lifetimes were evaluated by using (utilizing) Kethley SMU 236 and PR650. The half-life was a length of time required for the brightness to deteriorate to 50% of the initial brightness after driving an OLED.

TABLE 2

| | Dopant in EML | Driving voltage (V) | Current density (mA/cm$^2$) | Brightness (cd/m$^2$) | Efficiency (cd/A) | Color of emitted light | Half-life lifetime (hr@100 mA/cm$^2$) |
|---|---|---|---|---|---|---|---|
| Example 1 | Compound 5 | 5.59 | 50 | 3280 | 6.56 | Blue | 320 |
| Example 2 | Compound 13 | 5.62 | 50 | 3250 | 6.50 | Blue | 345 |
| Example 3 | Compound 22 | 5.48 | 50 | 3420 | 6.84 | Blue | 350 |
| Example 4 | Compound 37 | 5.50 | 50 | 3410 | 6.82 | Blue | 360 |
| Example 5 | Compound 52 | 5.65 | 50 | 3230 | 6.46 | Blue | 310 |
| Comparative Example 1 | Compound A | 7.01 | 50 | 2645 | 5.29 | Blue | 258 |

Referring to Table 2, it may be confirmed that the OLEDs prepared in Examples 1 to 5 have excellent performance in terms of all of the driving voltage, the brightness, the efficiency, and the half-life lifetime, compared to those of the OLED prepared in Comparative Example 1.

As described above, according to the one or more of the above embodiments of the present invention, an OLED including the condensed cyclic compound may have a low drying voltage, a high efficiency, a high brightness, and/or a long lifespan.

It should be understood that the example embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the drawing, it will be understood by those of ordinary skill in the art that various changes in form and details may be made therein without departing from the spirit and scope of the present invention as defined by the following claims, and equivalents thereof.

What is claimed is:

1. A condensed cyclic compound represented by Formula 1:

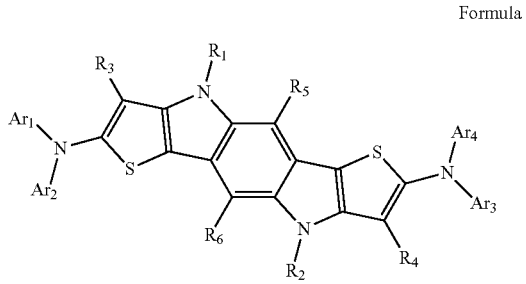

Formula 1 wherein, in Formula 1, $Ar_1$ to $Ar_4$ are each independently selected from a substituted or unsubstituted $C_6$-$C_{30}$ aryl group, a substituted or unsubstituted $C_4$-$C_{30}$ heteroaryl group, and a substituted or unsubstituted monovalent $C_6$-$C_{30}$ non-aromatic condensed polycyclic group;

$R_1$ and $R_2$ are each independently selected from a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, —Si($Q_1$)($Q_2$)($Q_3$), and —B($Q_4$)($Q_5$);

$R_3$ to $R_6$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, —Si($Q_1$)($Q_2$)($Q_3$), and —B($Q_4$)($Q_5$), wherein at least one substituent of the substituted $C_1$-$C_{10}$ alkyl group, substituted $C_2$-$C_{10}$ alkenyl group, substituted $C_2$-$C_{10}$ alkynyl group, substituted $C_1$-$C_{10}$ alkoxy group, substituted $C_3$-$C_{10}$ cycloalkyl group, substituted $C_3$-$C_{10}$ cycloalkenyl group, substituted $C_3$-$C_{10}$ heterocycloalkyl group, substituted $C_3$-$C_{10}$ heterocycloalkenyl group, substituted $C_6$-$C_{30}$ aryl group, substituted $C_2$-$C_{30}$ heteroaryl group, substituted $C_6$-$C_{30}$ aryloxy group, and substituted $C_6$-$C_{30}$ arylthio group is selected from:

a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{21}$)($Q_{22}$), —Si($Q_{23}$)($Q_{24}$)($Q_{25}$), and —B($Q_{26}$)($Q_{27}$); and —Si($Q_{31}$)($Q_{32}$)($Q_{33}$) and —B($Q_{34}$)($Q_{35}$);

$Q_1$ to $Q_5$, $Q_{11}$ to $Q_{17}$, $Q_{21}$ to $Q_{27}$, and $Q_{31}$ to $Q_{37}$ are each independently selected from a hydrogen atom, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

2. The condensed cyclic compound of claim 1, wherein $Ar_1$ to $Ar_4$ are each independently selected from:

a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_4$-$C_{30}$ heteroaryl group, a $C_6$-$C_{30}$ aryloxy group, and a $C_6$-$C_{30}$ arylthio group and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group.

3. The condensed cyclic compound of claim 1, wherein $Ar_1$ to $Ar_4$ are each independently a condensed cyclic compound represented by one of Formulae 3A to 3R:

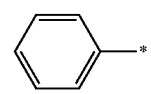

3A

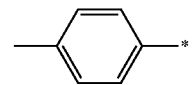

3B

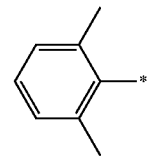

3C

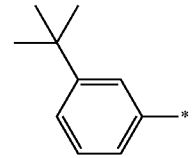

3D

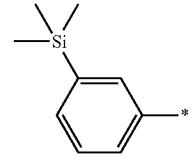

3E

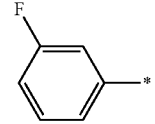

3F

-continued

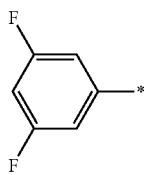 3G

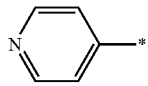 3H

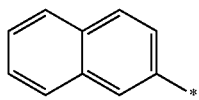 3I

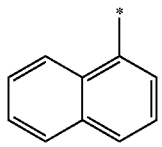 3J

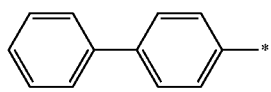 3K

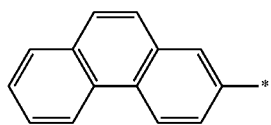 3L

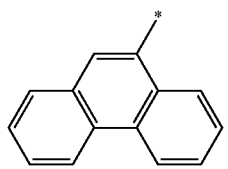 3M

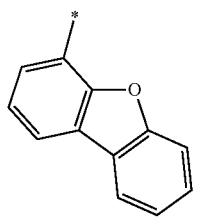 3N

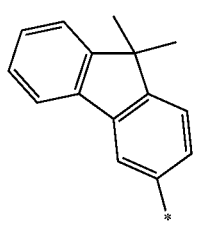 3O

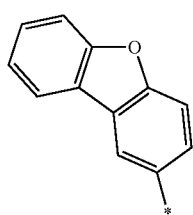 3P

-continued

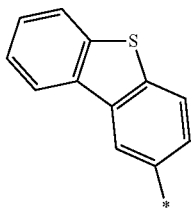 3Q

3R

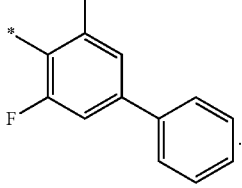

4. The condensed cyclic compound of claim 1, wherein $R_1$ and $R_2$ are each independently selected from:

a methyl group, an ethyl group, a propyl group, a butyl group, a pentyl group, a hexyl group, a heptyl group, an octyl group, a nonyl group, a decyl group, a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group;

a methyl group, an ethyl group, a propyl group, a butyl group, a pentyl group, a hexyl group, a heptyl group, an octyl group, a nonyl group and a decyl group, each substituted with at least one of a deuterium atom, a halogen atom, a hydroxyl group, a cyano group, a nitro group, and an amino group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl group, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyran group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group, each substituted with at least one of a deuterium atom, a halogen atom, a hydroxyl group, a cyano group, a nitro group, an amino group, a carboxyl group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_4$-$C_{30}$ heteroaryl group, a $C_6$-$C_{30}$ aryloxy group, a $C_6$-$C_{30}$ arylthio group, and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group.

5. The condensed cyclic compound of claim 1, wherein $R_1$ and $R_2$ are each independently selected from an ethyl group, a butyl group, and a condensed cyclic compound represented by one of Formulae 4A to 4C:

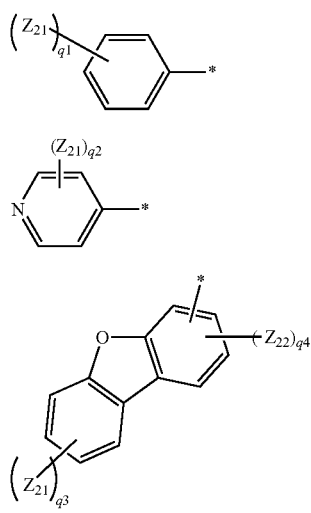

wherein, in Formulae 4A to 4C,
$Z_{21}$ and $Z_{22}$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{20}$ aryl group, a $C_4$-$C_{20}$ heteroaryl group, and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group;

q1 is an integer selected from 1 to 5;
q2 is an integer selected from 1 to 4;
q3 is an integer selected from 1 to 4;
q4 is an integer selected from 1 to 3; and
* is a binding site.

6. The condensed cyclic compound of claim 1, wherein $R_1$ and $R_2$ are each independently selected from an ethyl group, a tert-butyl group, and a condensed cyclic compound represented by one of Formulae 5A to 5D:

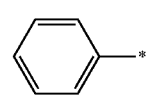

5A

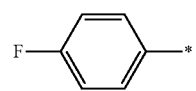

5B

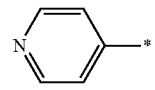

5C

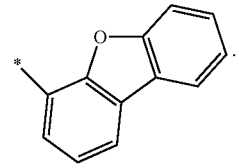

5D

7. The condensed cyclic compound of claim 1, wherein $R_3$ to $R_6$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, and —Si($Q_1$)($Q_2$)($Q_3$) where $Q_1$ to $Q_3$ are each independently selected from a hydrogen atom, a $C_1$-$C_{10}$ alkyl group, a $C_1$-$C_{10}$ alkoxy group, and a $C_6$-$C_{20}$ aryl group.

8. The condensed cyclic compound of claim 1, wherein $Ar_1$ to $Ar_4$ are each independently a condensed cyclic compound represented by one of Formulae 2A to 2D:

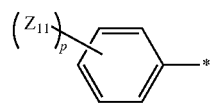

2A

-continued

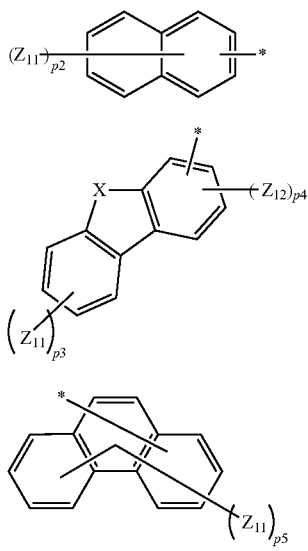

wherein, in Formulae 2A to 2D,
X is O, S, or C($Z_{12}$)($Z_{13}$);
$Z_{11}$ to $Z_{13}$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{30}$ aryl group, a $C_4$-$C_{30}$ heteroaryl group, and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group;
p1 is an integer selected from 1 to 5;
p2 is an integer selected from 1 to 7;
p3 is an integer selected from 1 to 4;
p4 is an integer selected from 1 to 3;
p5 is an integer selected from 1 to 9; and
\* is a binding site.

9. The condensed cyclic compound of claim 8, wherein at least one of $Ar_1$ to $Ar_4$ is a condensed cyclic compound represented by one of Formulae 2C or 2D,
wherein, in Formulae 2C and 2D,
X is O;
$Z_{11}$ to $Z_{12}$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{30}$ aryl group, a $C_4$-$C_{30}$ heteroaryl group, and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group;
p3 is an integer selected from 1 to 4;
p4 is an integer selected from 1 to 3;
p5 is an integer selected from 1 to 9; and
\* is a binding site.

10. The condensed cyclic compound of claim 1, wherein the condensed cyclic compound is represented by Formula 1A:

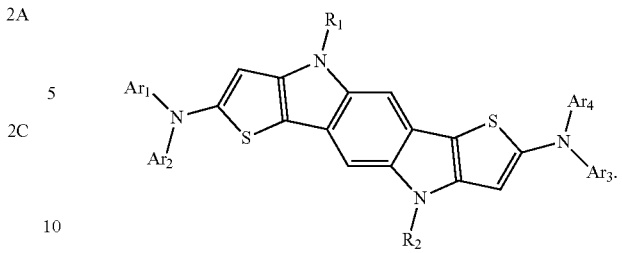

Formula 1A

11. The condensed cyclic compound of claim 10, wherein:
$Ar_1$ to $Ar_4$ are each independently selected from Formulae 2A to 2D, and
$R_1$ and $R_2$ are each independently selected from an ethyl group, a butyl group, and a condensed cyclic compound represented by one of Formulae 4A to 4C:

2A

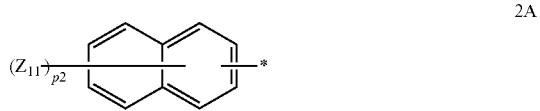
2A

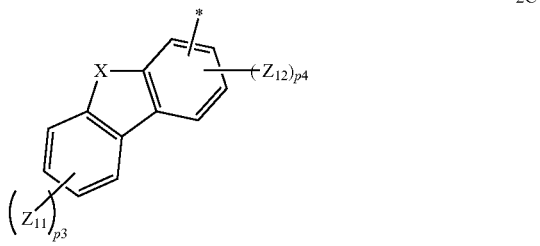
2C

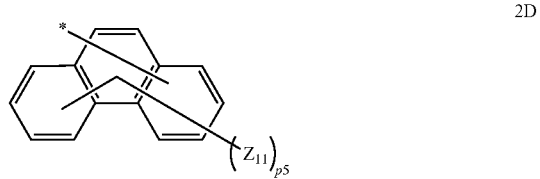
2D

4A

4A

4C wherein in Formulae 2A to 2D,
X is O, S, or C($Z_{12}$)($Z_{13}$);

$Z_{11}$ to $Z_{13}$ are each independently a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{30}$ aryl group, a $C_4$-$C_{30}$ heteroaryl group, and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group;

p1 is an integer selected from 1 to 5;

p2 is an integer selected from 1 to 7;

p3 is an integer selected from 1 to 4;

p4 is an integer selected from 1 to 3;

p5 is an integer selected from 1 to 9;

in Formulae 4A to 4C, $Z_{21}$ and $Z_{22}$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{20}$ aryl group, a $C_4$-$C_{20}$ heteroaryl group, and —Si($Q_{31}$)($Q_{32}$)($Q_{33}$) where $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group;

q1 is an integer selected from 1 to 5;

q2 is an integer selected from 1 to 4;

q3 is an integer selected from 1 to 4;

q4 is an integer selected from 1 to 3; and

* is a binding site.

12. The condensed cyclic compound of claim 10, wherein $Ar_1$ to $Ar_4$ are each independently selected from Formulae 3A to 3R;

$R_1$ and $R_2$ are each independently selected from an ethyl group, a butyl group, and a condensed cyclic compound represented by one selected from Formulae 5A to 5D:

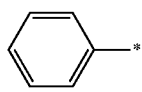
3A

3B

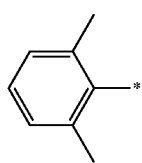
3C

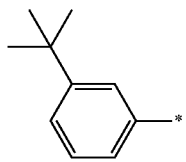
3D

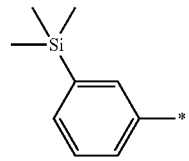
3E

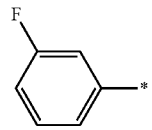
3F

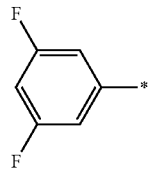
3G

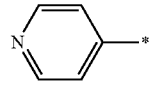
3H

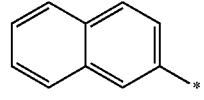
3I

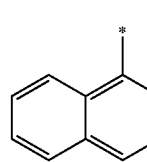
3J

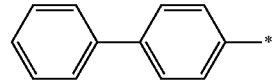
3K

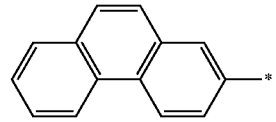
3L

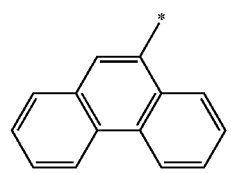
3M

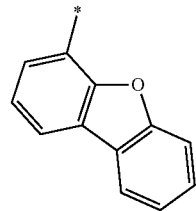
3N

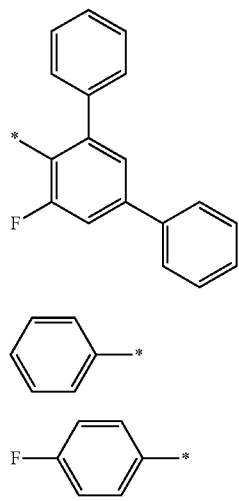
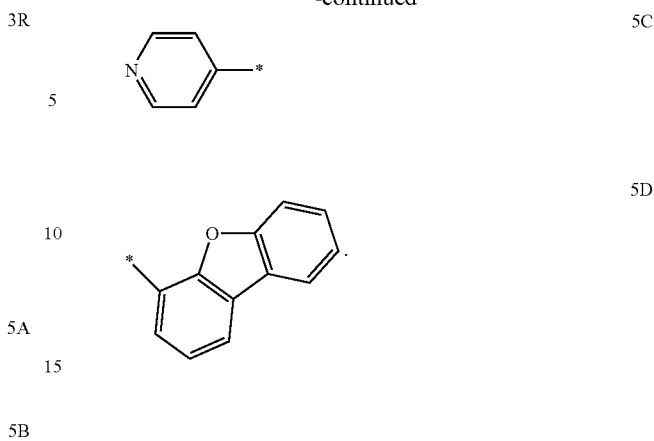
13. The condensed cyclic compound of claim 1, wherein the condensed cyclic compound is represented by one of Compounds 1 to 16:
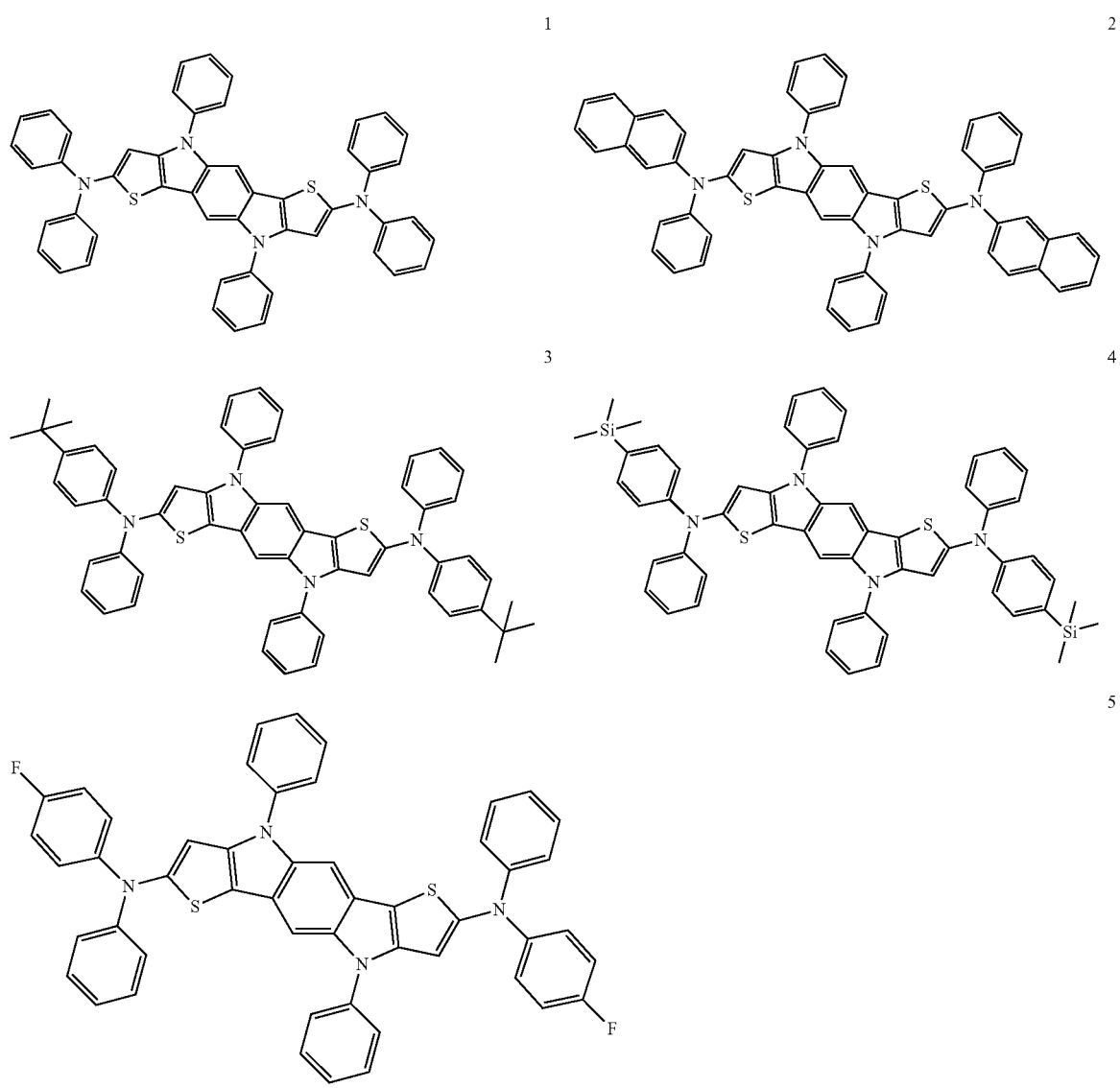

6
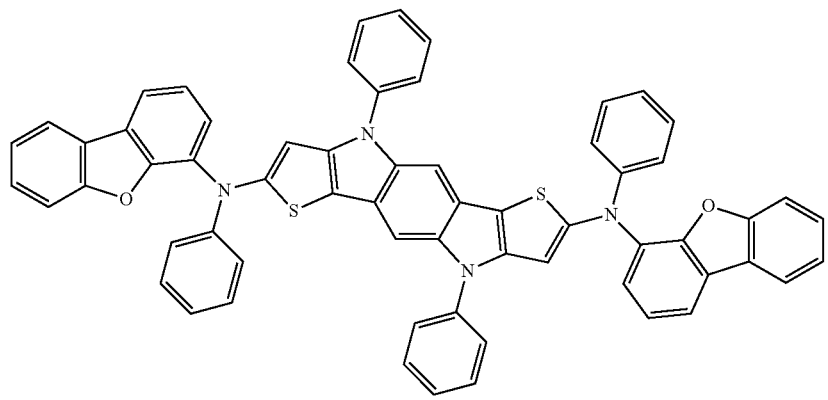
7
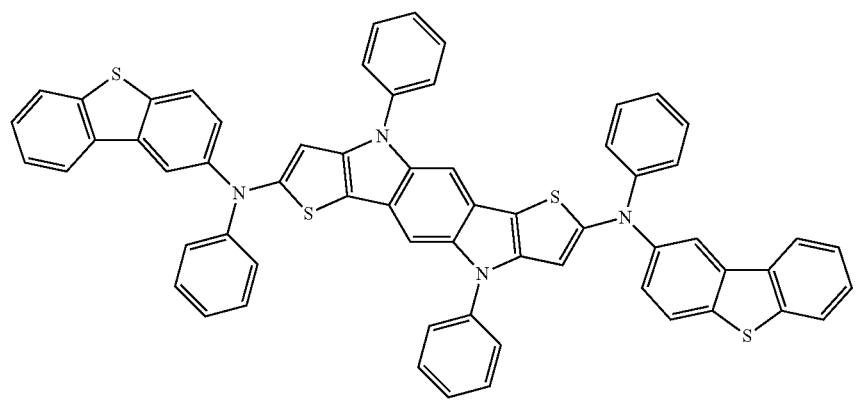
8
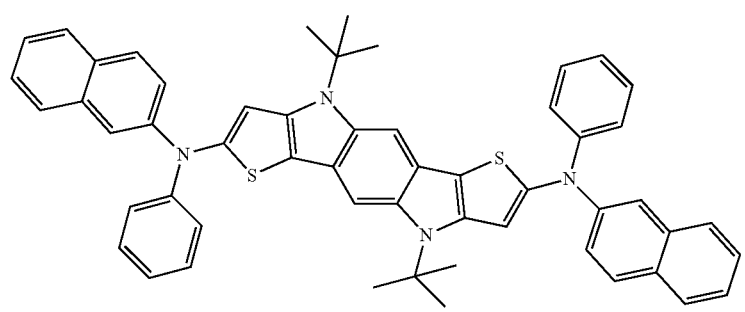
9
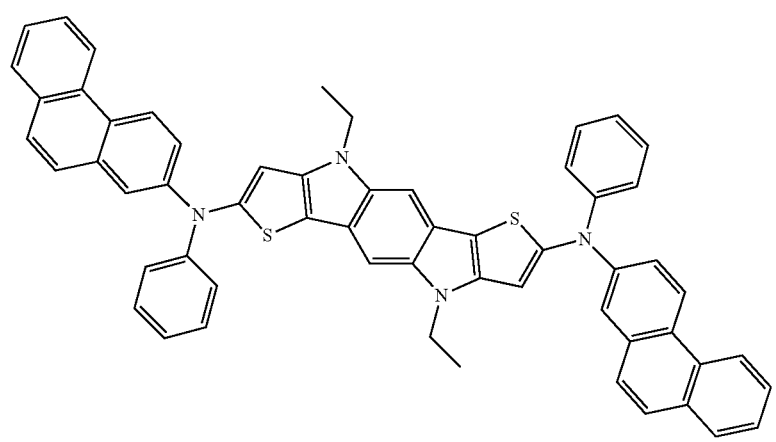

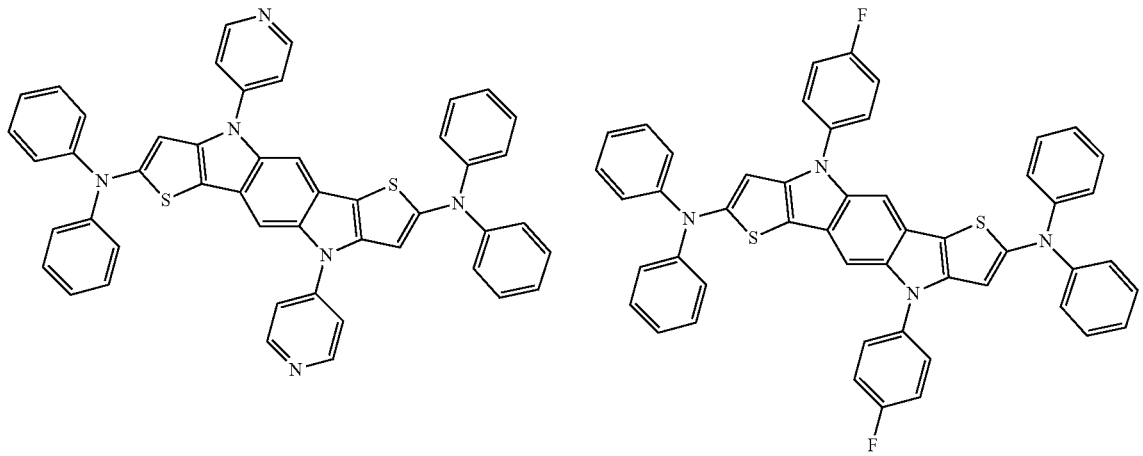
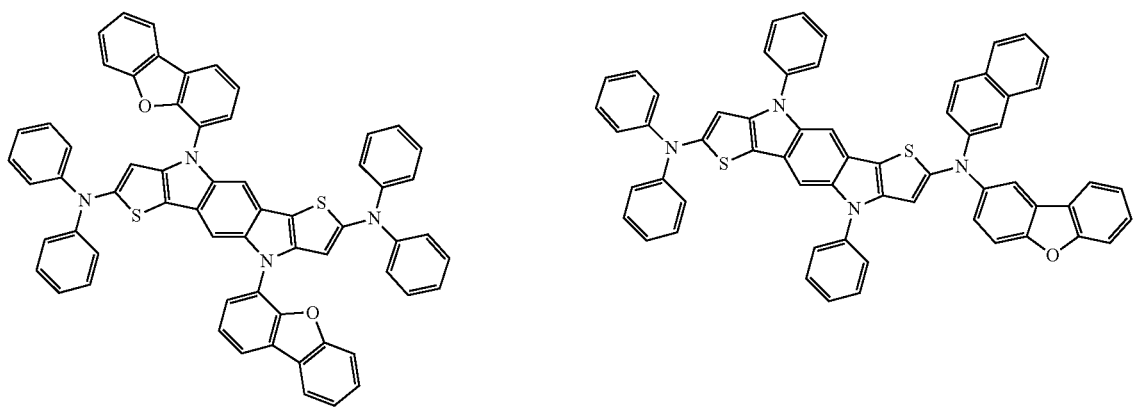
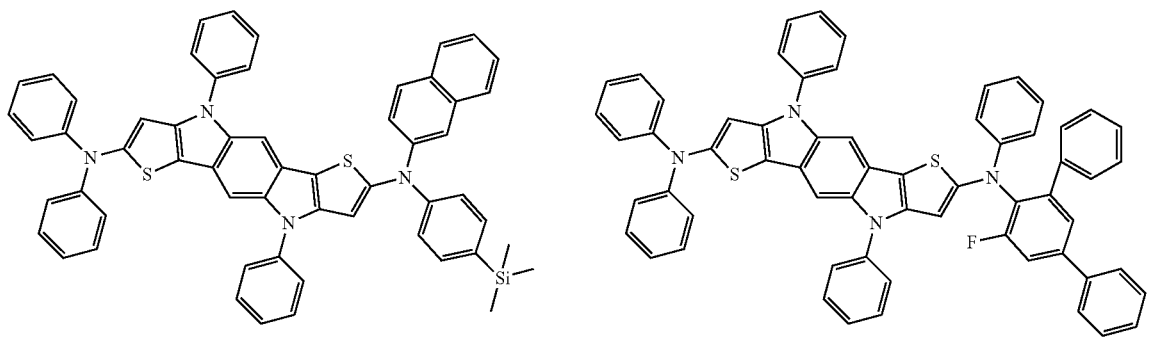

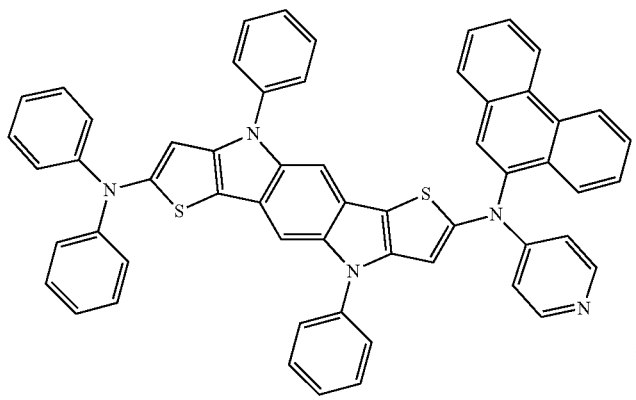

14. The condensed cyclic compound of claim 13, wherein the condensed cyclic compound is represented by one of Compounds 3, 6, 9, and 15.

15. An organic light-emitting diode (OLED) comprising:
a first electrode;
a second electrode facing the first electrode; and
an organic layer between the first electrode and the second electrode, and comprising an emission layer,
wherein the organic layer comprises at least one of the condensed cyclic compounds of claim 1.

16. The OLED of claim 15, wherein the organic layer further comprises:
a hole transport region between the first electrode and the emission layer; and
an electron transport region between the emission layer and the second electrode.

17. The OLED of claim 16, wherein the electron transport region comprises at least one of a hole blocking layer, an electron transport layer, and an electron injection layer.

18. The OLED of claim 16, wherein the hole transport region comprises at least one of an electron blocking layer, a hole transport layer, and a hole injection layer.

19. The OLED of claim 16, wherein the emission layer comprises the condensed cyclic compound.

20. The OLED of claim 16, wherein the hole transport region comprises the condensed cyclic compound.

* * * * *